(12) United States Patent
Cadwell

(10) Patent No.: US 10,039,461 B2
(45) Date of Patent: *Aug. 7, 2018

(54) NEUROMONITORING SYSTEMS AND METHODS

(71) Applicant: Cadwell Laboratories Inc., Kennewick, WA (US)

(72) Inventor: John Cadwell, Kennewick, WA (US)

(73) Assignee: Cadwell Laboratories, Inc., Kennewick, WA (US)

(*) Notice: Subject to any disclaimer, the term of this patent is extended or adjusted under 35 U.S.C. 154(b) by 101 days.

This patent is subject to a terminal disclaimer.

(21) Appl. No.: 15/056,681

(22) Filed: Feb. 29, 2016

(65) Prior Publication Data

US 2016/0174861 A1 Jun. 23, 2016

Related U.S. Application Data

(63) Continuation of application No. 14/092,083, filed on Nov. 27, 2013, now Pat. No. 9,295,401.

(Continued)

(51) Int. Cl.
*A61B 5/00* (2006.01)
*A61B 5/04* (2006.01)
(Continued)

(52) U.S. Cl.
CPC ........ *A61B 5/04001* (2013.01); *A61B 5/0488* (2013.01); *A61B 5/0492* (2013.01);
(Continued)

(58) Field of Classification Search
CPC . A61B 5/0488; A61B 5/04001; A61B 5/4041; A61B 5/4893; A61B 2505/05; A61B 5/053
See application file for complete search history.

(56) References Cited

U.S. PATENT DOCUMENTS

| 751,475 A | 2/1904 | De Vilbiss |
|---|---|---|
| 2,320,709 A | 6/1943 | Arnesen |

(Continued)

FOREIGN PATENT DOCUMENTS

| EP | 298268 | 1/1989 |
|---|---|---|
| EP | 890341 | 1/1999 |

(Continued)

OTHER PUBLICATIONS

Aage R. Møller, "Intraoperative Neurophysiologic Monitoring", University of Pittsburgh, School of Medicine Pennsylvania, © 1995 by Harwood Academic Publishers GmbH.

(Continued)

*Primary Examiner* — Max Hindenburg
(74) *Attorney, Agent, or Firm* — Novel IP

(57) ABSTRACT

Systems, devices, and methods are described for neuromonitoring. A minimum stimulus signal required to elicit a threshold neuromuscular response is determined by delivery of stimulus signals to tissue and detection of neuromuscular responses in muscle tissue. The strength of the delivered stimulus signals is varied, for example by adjusting the current amplitude or pulse width of the signals, and muscle responses are measure, for example by detecting EMG signals. The delivered stimuli and corresponding responses are then used to determine a stimulation threshold. The stimulation threshold may be used to indicate at least one of nerve proximity and pedicle integrity.

26 Claims, 25 Drawing Sheets

Related U.S. Application Data

(60) Provisional application No. 61/730,202, filed on Nov. 27, 2012.

(51) Int. Cl.
  *A61B 5/0488* (2006.01)
  *A61B 5/053* (2006.01)
  *A61B 5/0492* (2006.01)
  *A61N 1/20* (2006.01)

(52) U.S. Cl.
  CPC ............ *A61B 5/053* (2013.01); *A61B 5/4041* (2013.01); *A61B 5/4893* (2013.01); *A61B 5/7246* (2013.01); *A61B 5/7278* (2013.01); *A61B 5/742* (2013.01); *A61N 1/20* (2013.01); *A61B 2505/05* (2013.01)

(56) References Cited

U.S. PATENT DOCUMENTS

| | | |
|---|---|---|
| 2,807,259 A | 9/1957 | Guerriero |
| 3,682,162 A | 8/1972 | Colyer |
| 3,985,125 A | 10/1976 | Rose |
| 4,155,353 A | 5/1979 | Rea |
| 4,263,899 A | 4/1981 | Burgin |
| 4,545,374 A | 10/1985 | Jacobson |
| 4,562,832 A | 1/1986 | Wilder |
| 4,616,635 A | 10/1986 | Caspar |
| 4,705,049 A | 11/1987 | John |
| 4,716,901 A | 1/1988 | Jackson |
| 4,765,311 A | 8/1988 | Kulik |
| 4,817,587 A | 4/1989 | Janese |
| 4,862,891 A | 9/1989 | Smith |
| 5,171,279 A | 12/1992 | Mathews |
| 5,196,015 A | 3/1993 | Neubardt |
| 5,284,153 A | 2/1994 | Raymond |
| 5,284,154 A | 2/1994 | Raymond |
| 5,299,563 A | 4/1994 | Seton |
| 5,377,667 A | 1/1995 | Patton |
| 5,472,426 A | 12/1995 | Bonati |
| 5,474,558 A | 12/1995 | Neubardt |
| 5,540,235 A | 7/1996 | Wilson |
| 5,565,779 A | 10/1996 | Arakawa |
| 5,601,608 A | 2/1997 | Mouchawar |
| 5,681,265 A | 10/1997 | Maeda |
| 5,728,046 A | 3/1998 | Mayer |
| 5,741,261 A | 4/1998 | Moskovitz |
| 5,772,661 A | 6/1998 | Michelson |
| 5,775,331 A | 7/1998 | Raymond |
| 5,785,648 A | 7/1998 | Min |
| 5,792,044 A | 8/1998 | Foley |
| 5,795,291 A | 8/1998 | Koros |
| 5,830,150 A | 11/1998 | Palmer |
| 5,860,973 A | 1/1999 | Michelson |
| 5,868,668 A | 2/1999 | Weiss |
| 5,885,210 A | 3/1999 | Cox |
| 5,891,147 A | 4/1999 | Moskovitz |
| 5,928,139 A | 7/1999 | Koros |
| 5,928,158 A | 7/1999 | Aristides |
| 5,931,777 A | 8/1999 | Sava |
| 5,944,658 A | 8/1999 | Koros |
| 5,954,635 A | 9/1999 | Foley |
| 5,993,385 A | 11/1999 | Johnston |
| 6,004,312 A | 12/1999 | Finneran |
| 6,004,341 A | 12/1999 | Zhu |
| 6,042,540 A | 3/2000 | Johnston |
| 6,074,343 A | 6/2000 | Nathanson |
| 6,095,987 A | 8/2000 | Shmulewitz |
| 6,139,493 A | 10/2000 | Koros |
| 6,152,871 A | 11/2000 | Foley |
| 6,181,961 B1 | 1/2001 | Prass |
| 6,196,969 B1 | 3/2001 | Bester |
| 6,206,826 B1 | 3/2001 | Mathews |
| 6,224,545 B1 | 5/2001 | Cocchia |
| 6,259,945 B1 | 7/2001 | Epstein |
| 6,266,558 B1 | 7/2001 | Gozani |
| 6,287,322 B1 | 9/2001 | Zhu |
| 6,302,842 B1 | 10/2001 | Auerbach |
| 6,306,100 B1 | 10/2001 | Prass |
| 6,309,349 B1 | 10/2001 | Bertolero |
| 6,325,764 B1 | 12/2001 | Griffith |
| 6,334,068 B1 | 12/2001 | Hacker |
| 6,425,859 B1 | 7/2002 | Foley |
| 6,450,952 B1 | 9/2002 | Rioux |
| 6,466,817 B1 | 10/2002 | Kaula |
| 6,500,128 B2 | 12/2002 | Marino |
| 6,712,795 B1 | 3/2004 | Cohen |
| 6,805,668 B1 | 10/2004 | Cadwell |
| 6,847,849 B2 | 1/2005 | Mamo |
| 6,851,430 B2 | 2/2005 | Tsou |
| 6,870,109 B1 | 3/2005 | Villarreal |
| 6,926,728 B2 | 8/2005 | Zucherman |
| 6,945,933 B2 | 9/2005 | Branch |
| 7,072,521 B1 | 7/2006 | Cadwell |
| 7,089,059 B1 | 8/2006 | Pless |
| 7,177,677 B2 | 2/2007 | Kaula |
| 7,214,197 B2 | 5/2007 | Prass |
| 7,230,688 B1 | 6/2007 | Villarreal |
| 7,261,688 B2 | 8/2007 | Smith |
| 7,374,448 B1 | 5/2008 | Jepsen |
| 7,470,236 B1 | 12/2008 | Kelleher |
| 7,801,601 B2* | 9/2010 | Maschino ............... A61N 2/008 607/2 |
| 7,914,350 B1 | 3/2011 | Bozich |
| 7,963,927 B2 | 6/2011 | Kelleher |
| 8,192,437 B2 | 6/2012 | Simonson |
| D670,656 S | 11/2012 | Jepsen |
| 8,323,208 B2* | 12/2012 | Davis ................. A61B 5/04001 600/546 |
| 8,876,813 B2 | 11/2014 | Min |
| 8,942,797 B2 | 1/2015 | Bartol |
| 8,958,869 B2 | 2/2015 | Kelleher |
| 9,084,551 B2 | 7/2015 | Brunnett |
| 9,155,503 B2 | 10/2015 | Cadwell |
| 9,295,401 B2* | 3/2016 | Cadwell ............. A61B 5/04001 |
| 9,352,153 B2* | 5/2016 | van Dijk ............... A61N 1/0541 |
| 9,730,634 B2 | 8/2017 | Cadwell |
| 2014/0121555 A1 | 5/2014 | Scott |
| 2014/0275926 A1 | 9/2014 | Scott |
| 2016/0000382 A1 | 1/2016 | Jain |
| 2016/0174861 A1 | 6/2016 | Cadwell |

FOREIGN PATENT DOCUMENTS

| | | |
|---|---|---|
| EP | 972538 | 1/2000 |
| WO | 2000038574 A1 | 7/2000 |
| WO | 2000066217 A1 | 11/2000 |
| WO | 2001037728 A1 | 5/2001 |
| WO | 2003005887 A2 | 1/2003 |
| WO | 2005030318 A1 | 4/2005 |
| WO | 2006042241 A2 | 4/2006 |

OTHER PUBLICATIONS

Bergey et al., "Endoscopic Lateral Transpsoas Approach to the Lumbar Spine", SPINE 29 (15):1681-1688 (2004).

Bertagnoli, et. al., "The AnteroLateral transPsoatic Approach (ALPA), A New Technique for Implanting Prosthetic Disc-Nucleus Devices", 16 (4):398-404 (2003).

Bose, et. al., "Neurophysiologic Monitoring of Spinal Nerve Root Function During Instrumented Posterior Lumbar Spine Surgery", 27 (13):1440-1450 (2002).

Butterworth et. al., "Effects of Halothane and Enflurane on Firing Threshold of Frog Myelinated Axon", Journal of Physiology 411:493-516, (1989) From the Anesthesia Research Labs, Brigham and Women's Hospital, Harvard Medical School, 75 Francis St., Boston, MA 02115, jp.physoc.org.

Calancie, et. al., "Threshold-level multipulse transcranial electrical stimulation of motor cortex for intraoperative monitoring of spinal motor tracts: description of method and comparison to somatosensory evoked potential monitoring" J Neurosurg 88:457-470 (1998).

(56) References Cited

OTHER PUBLICATIONS

Calancie, et. al., "Threshold-level repetitive transcranial electrical stimulation for intraoperative monitoring of central motor conduction", J. Neurosurg 95:161-168 (2001).

Calancie, et. al., Stimulus-Evoked EMG Monitoring During Transpedicular Lumbosacral Spine Instrumentation, Initial Clinical Results, 19 (24):2780-2786 (1994).

Carl T. Brighton, "Clinical Orthopaedics and Related Research", Clinical Orthopaedics and related research No. 384, pp. 82-100 (2001).

Clements, et. al., "Evoked and Spontaneous Electromyography to Evaluate Lumbosacral Pedicle Screw Placement", 21 (5):600-604 (1996).

Danesh-Clough, et. al., "The Use of Evoked EMG in Detecting Misplaced Thoracolumbar Pedicle Screws", 26 (12):1313-1316 (2001).

Dezawa et al., "Retroperitoneal Laparoscopic Lateral Approach to the Lumbar Spine: A New Approach, Technique, and Clinical Trial", Journal of Spinal Disorders 13(2):138-143 (2000).

Dickman, et al., "Techniques in Neurosurgery", National Library of Medicine, 3 (4) 301-307 (1997).

Epstein, et al., "Evaluation of Intraoperative Somatosensory-Evoked Potential Monitoring During 100 Cervical Operations", 18(6):737-747 (1993), J.B. Lippincott Company.

Glassman, et. al., "A Prospective Analysis of Intraoperative Electromyographic Monitoring of Pedicle Screw Placement with Computed Tomographic Scan Confirmation", 20(12):1375-1379. 2012.

Goldstein, et. al., "Minimally Invasive Endoscopic Surgery of the Lumbar Spine", Operative Techniques in Orthopaedics, 7 (1):27-35 (1997).

Greenblatt, et. al., "Needle Nerve Stimulator-Locator", 41 (5):599-602 (1962).

H.M. Mayer, "Minimally Invasive Spine Surgery, A Surgical Manual", Chapter 12, pp. 117-131 (2000).

Hinrichs, et al., "A trend-detection algorithm for intraoperative EEG monitoring", Med. Eng. Phys. 18 (8):626-631 (1996).

Holland, "Spine Update, Intraoperative Electromyography During Thoracolumbar Spinal Surgery", 23 (17):1915-1922 (1998).

Holland, et al., "Continuous Electromyographic Monitoring to Detect Nerve Root Injury During Thoracolumbar Scoliosis Surgery", 22 (21):2547-2550 (1997), Lippincott-Raven Publishers.

Hovey, A Guide to Motor Nerve Monitoring, pp. 1-31 Mar. 20, 1998, The Magstim Company Limited.

Kevin T. Foley, et. al., "Microendoscipic Discectomy" Techniques in Neurosurgery, 3:(4):301-307, © 1997 Lippincott-Raven Publishers, Philadelphia.

Kossmann et al., "The use of a retractor system (SynFrame) for open, minimal invasive reconstruction of the anterior column of the thoracic and lumbar spine", 10:396-402 (2001).

Kossmann, et. al., "Minimally Invasive Vertebral Replacement with Cages in Thoracic and Lumbar Spine", European Journal of Trauma, 2001, No. 6, pp. 292-300.

Lenke, et. al., "Triggered Electromyographic Threshold for Accuracy of Pedicle Screw Placement, An Animal Model and Clinical Correlation", 20 (14):1585-1591 (1995).

Lomanto et al., "7th World Congress of Endoscopic Surgery" Singapore, Jun. 1-4, 2000 Monduzzi Editore S.p.A.; email: monduzzi@monduzzi.com, pp. 97-103 and 105-111.

MaGuire, et. al., "Evaluation of Intrapedicular Screw Position Using Intraoperative Evoked Electromyography", 20 (9):1068-1074 (1995).

Mathews et al., "Laparoscopic Discectomy With Anterior Lumbar Interbody Fusion, A Preliminary Review", 20 (16):1797-1802, (1995), Lippincott-Raven Publishers.

Michael R. Isley, et. al., "Recent Advances in Intraoperative Neuromonitoring of Spinal Cord Function: Pedicle Screw Stimulation Techniques", Am. J. End Technol. 37:93-126 (1997).

Minahan, et. al., "The Effect of Neuromuscular Blockade on Pedicle Screw Stimulation Thresholds" 25(19):2526-2530 (2000).

Pimenta et. al., "Implante de prótese de núcleo pulposo: análise inicial", J Bras Neurocirurg 12 (2):93-96, (2001).

Raymond J. Gardocki, MD, "Tubular diskectomy minimizes collateral damage", AAOS Now, Sep. 2009 Issue, http://www.aaos.org/news/aaosnow/sep09/clinical12.asp.

Raymond, et. al., "The NerveSeeker: A System for Automated Nerve Localization", Regional Anesthesia 17:151-162 (1992).

Reidy, et. al., "Evaluation of electromyographic monitoring during insertion of thoracic pedicle screws", British Editorial Society of Bone and Joint Surgery 83 (7):1009-1014, (2001).

Rose et al., "Persistently Electrified Pedicle Stimulation Instruments in Spinal Instrumentation: Technique and Protocol Development", Spine: 22(3): 334-343 (1997).

Teresa Riordan "Patents; A businessman invents a device to give laparoscopic surgeons a better view of their worK", New York Times www.nytimes.com/2004/29/business/patents-businessman-invents-device-give-la (Mar. 2004).

Toleikis, et. al., "The usefulness of Electrical Stimulation for Assessing Pedicle Screw Placements", Journal of Spinal Disorders, 13 (4):283-289 (2000).

U.Schick, et. al., "Microendoscopic lumbar discectomy versus open surgery: an intraoperative EMG study", pp. 20-26, Published online: Jul. 31, 2001 © Springer-Verlag 2001.

Vaccaro, et. al., "Principles and Practice of Spine Surgery", Mosby, Inc. © 2003, Chapter 21, pp. 275-281.

Vincent C. Traynelis, "Spinal arthroplasty", Neurosurg Focus 13 (2):1-7. Article 10, (2002).

Welch, et. al., "Evaluation with evoked and spontaneous electromyography during lumbar instrumentation: a prospective study", J Neurosurg 87:397-402, (1997).

Digitimer Ltd., 37 Hydeway, Welwyn Garden City, Hertfordshire. AL7 3BE England, email:sales@digitimer.com, website: www.digitimer.com, "Constant Current High Voltage Stimulator, Model DS7A, For Percutaneous Stimulation of Nerve and Muscle Tissue".

* cited by examiner

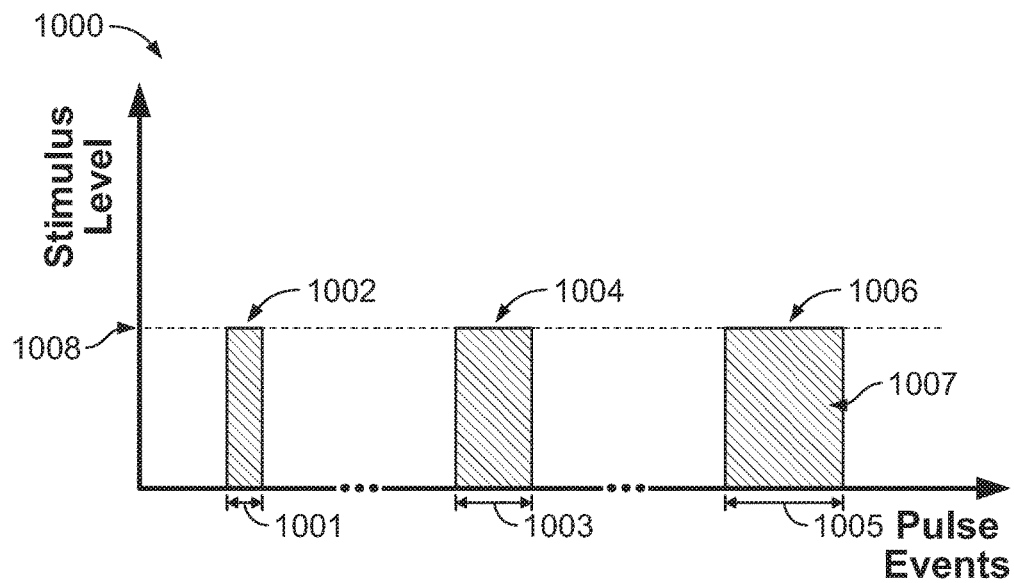
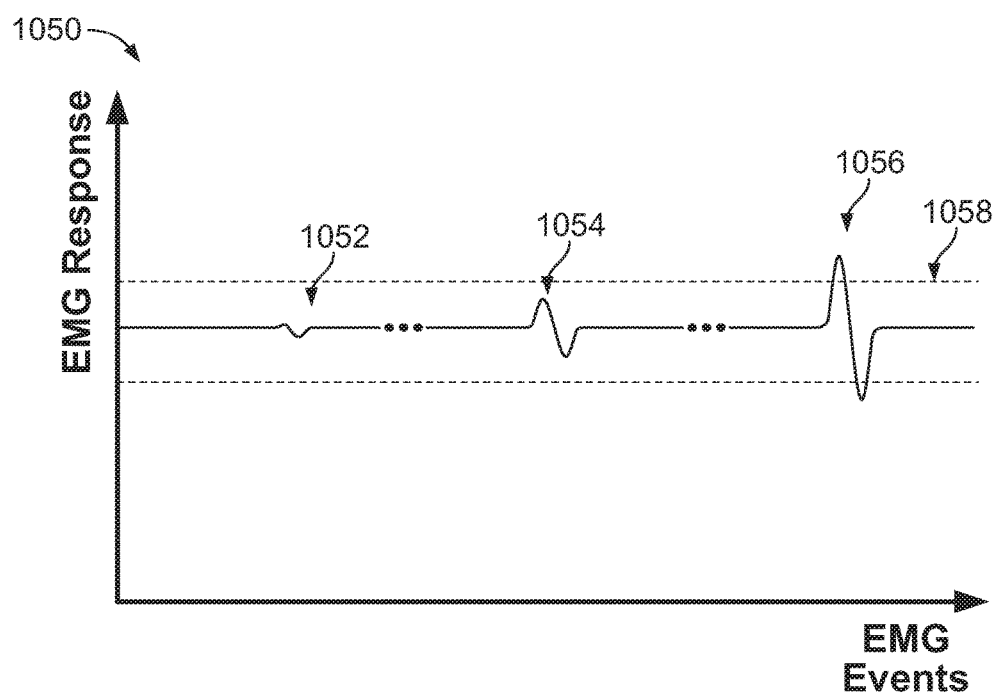
FIG. 15

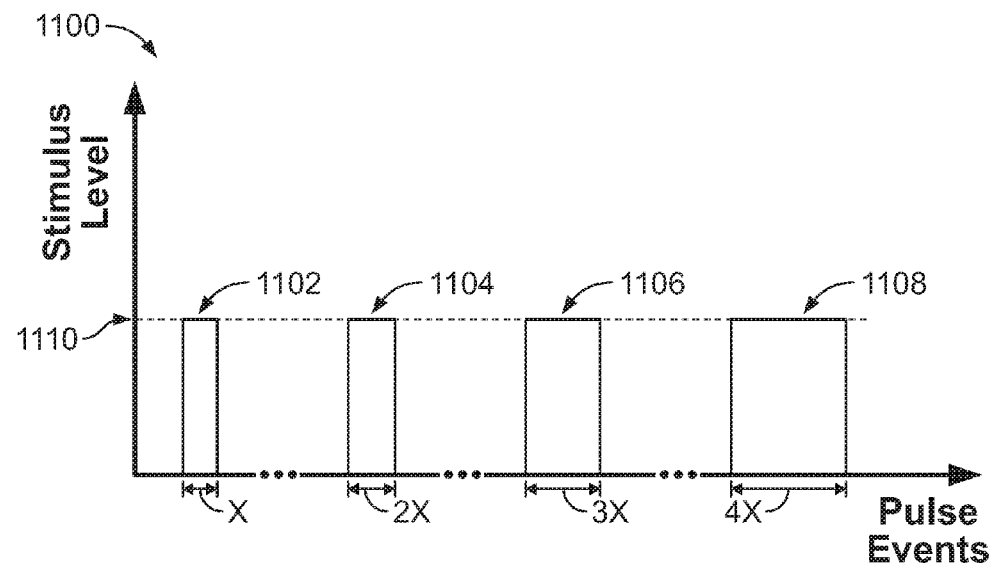
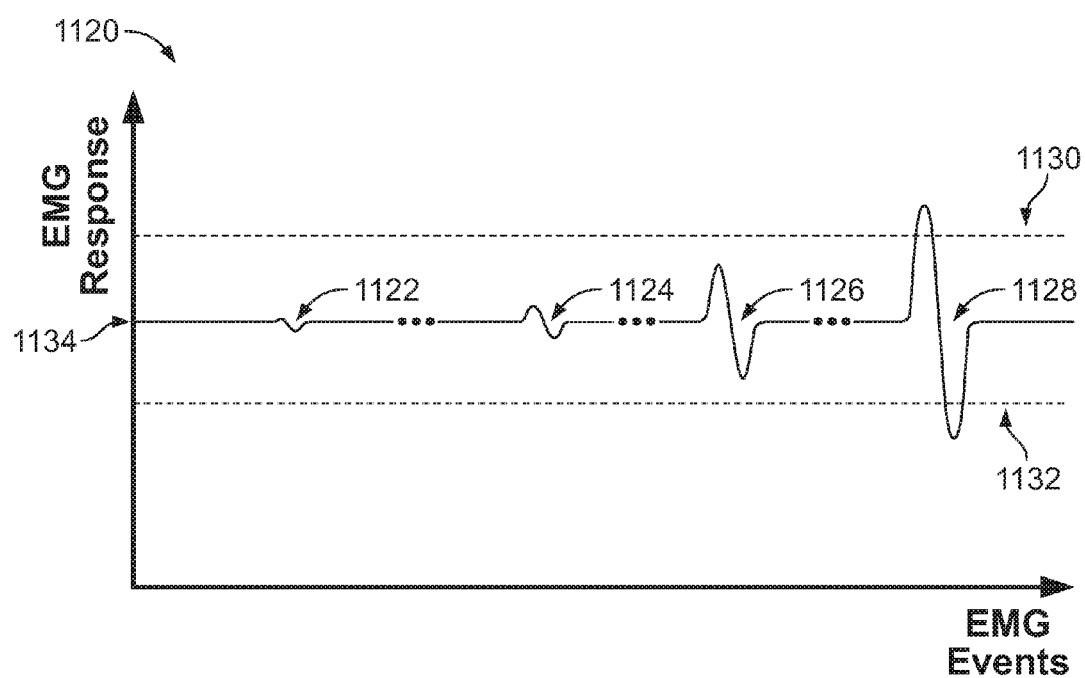
FIG. 16

Decreasing Threshold

| Indicators of Algorithm Status on Surgeon View | |
|---|---|
| No Stim<br>When the mode is running, but the stimulus loop is not closed (i.e., probe or instrument is not touching the patient), the dial indicates "No Stim." | 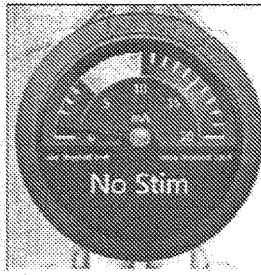 2260<br>FIG. 27 |
| Searching<br>When the stimulus loop is closed, but the algorithm has not yet identified a threshold, the dial indicates "Searching." | 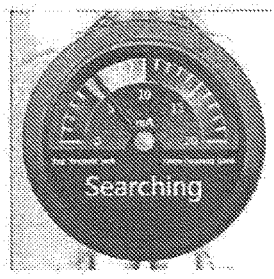 2270<br>FIG. 28 |
| > 20 mA<br>When the algorithm reaches it maximum stimulus intensity without identifying a threshold, the dial indicates "> MAX," where MAX is the maximum stimulus intensity for the mode (20 mA by default). | 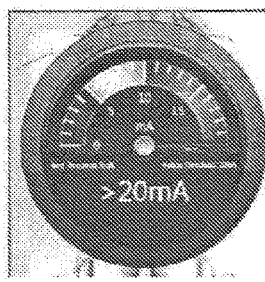 2280<br>FIG. 29 |
| Threshold Detected<br>When the algorithm has detected the minimum intensity required to produce a threshold crossing, it displays that intensity and adjusts the dial's background color as needed. | 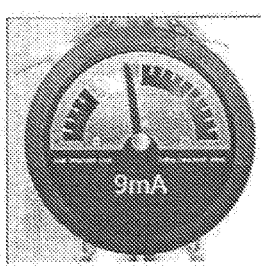 2290<br>FIG. 30 |

NEUROMONITORING SYSTEMS AND METHODS

CROSS-REFERENCE TO RELATED APPLICATIONS

This application is a continuation of U.S. patent application Ser. No. 14/092,083, filed Nov. 27, 2013 (now allowed), which claims the benefit under 35 U.S.C. § 119(e) of U.S. Provisional Application No. 61/730,202, filed Nov. 27, 2012, each of which is hereby incorporated by reference herein in its entirety.

BACKGROUND

The risk of injury to a nerve is a concern when performing surgical procedures, including minimally-invasive procedures, within close proximity to the spine or nerves. Surgeons increasingly rely on neuromonitoring techniques to monitor the nerves during such surgeries in order to avoid inadvertently injuring or contacting a nerve. Prior devices have been developed to help surgeons avoid contacting and damaging nerves during these procedures, but improvements are needed for enhancing the accuracy and speed of those devices.

Devices and methods are particularly needed for providing quick and safe neuromonitoring during surgery. Such devices should provide precise information regarding the proximity of nerves to surgical instruments or the integrity of vertebral bone quickly in order to provide early warning and avoid damage to the nerves. Both patient safety and the time required to provide the necessary information to the surgeon can be improved by reducing the number of electrical stimulations delivered to a patient or measurements that are required to produce an indication of nerve proximity or bone integrity.

SUMMARY

Disclosed herein are systems, devices, and methods for neuromonitoring, particularly neuromonitoring to avoid contacting or damaging nerves or causing patient discomfort during surgical procedures.

According to some implementations, a method for neuromonitoring is provided to identify by estimation the minimum current amplitude necessary to cause a muscle EMG response in a patient. In general, the method includes providing a plurality of stimulation pulses to patient anatomy near a desired surgical site, measuring the patient's response (e.g., neuromuscular response) to each of the pulses, and estimating from those responses the minimum current or other stimulation amount necessary to cause the response. In certain embodiments, each of the plurality of pulses is applied with sufficient energy to cause an EMG response in the patient. In certain applications that is achieved by adjusting the current amplitude, pulse width, or both, so as to deliver energy that exceeds an expected threshold energy level for the particular nerve or nerves in the region of the surgical site.

According to one aspect, a method for neuromonitoring includes the steps of (a) delivering a first stimulus signal having a first amplitude and a second stimulus signal having a second amplitude to tissue including or adjacent to a nerve, the first amplitude being different from the second amplitude; (2) detecting, in muscle tissue, a first neuromuscular response in response to the first stimulus signal and a second neuromuscular response in response to the second stimulus signal; (3) calculating a stimulation threshold for the nerve from the first and second stimulus signal amplitudes and the first and second neuromuscular responses, the stimulation threshold being an estimate of a minimum stimulus level required to elicit a neuromuscular response greater than or equal to a predetermined threshold; and (4) communicating to a user an indicator of the stimulation threshold to indicate at least one of nerve proximity and pedicle integrity. Additional stimulation signals may also be used.

In certain implementations, each of the first and second neuromuscular responses is greater than or equal to a predetermined threshold, while in other implementations one of the first and second neuromuscular responses is greater than or equal to the predetermined threshold, and the other of the first and second neuromuscular responses is less than the predetermined threshold. The first and second neuromuscular responses may be detected using EMG, and the predetermined threshold may correspond to a voltage level of detected EMG signals or may correspond to a level of correlation calculated from detected EMG signals. The method may include cross-correlating the detected EMG signals with an EMG response template (e.g., a predetermined template), and the predetermined threshold may be a level of correlation between the detected EMG signals and the EMG response template.

In certain implementations, the calculating step includes calculating a linear function from the first and second stimulus signal amplitudes and the first and second neuromuscular responses and determining the stimulation threshold from the linear function. In other implementations, the calculating step includes calculating a curve fit from the first and second stimulus signal amplitudes and the first and second neuromuscular responses and determining the stimulation threshold from the curve fit. The curve fit may be a sigmoid function, or may be another suitable function.

In certain implementations, the method further includes delivering a plurality of test stimulus signals to the tissue and detecting a plurality of test neuromuscular responses, each of the plurality of test neuromuscular responses corresponding to one of the plurality of test stimulus signals. Each of the plurality of test stimulus signals may have an amplitude that is greater than a preceding test stimulus signal, and the amplitudes of the test stimulus signals may increase at a constant increments or may increase at varying increments. The first and second stimulus signals may be selected based on the test stimulus signals and test neuromuscular responses. A curve fit may be calculated using the test stimulus signals and test neuromuscular responses. In certain implementations, the first and second stimulus signals are selected from test stimulus signals that elicit test neuromuscular responses that meet the predetermined threshold. In other implementations, one of the first and second stimulus signals is selected from test stimulus signals that elicit test neuromuscular responses that are greater than or equal to the predetermined threshold, and the other of the first and second stimulus signals is selected from test stimulus signals that do not elicit test neuromuscular responses that are greater than or equal to the predetermined threshold.

In certain implementations, detecting the first and second neuromuscular responses includes measuring neuromuscular activity in the muscle tissue during predetermined time windows, and the time windows may be offset from delivery times of the first and second stimulus signals. The predetermined time windows may be offset based on a signal transit time associated with the nerve and the muscle tissue.

In certain implementations, the first neuromuscular response is detected before the second stimulus signal is delivered, and the amplitude of the second stimulus signal may be adjusted based on the first neuromuscular response. In other implementations, the second stimulus signal is delivered before the first neuromuscular response is detected, and delivery of the first and second stimulus signals may be offset by an amount that is greater than or equal to a refractory period of the nerve and the muscle tissue. In certain implementations, the amplitude of the second stimulation signal may be double the amplitude of the first stimulation signal.

In certain implementations, the communicating step includes displaying the indicator for one of nerve proximity or pedicle integrity. The indicator may include a color-coded indicator that indicates one range of a plurality of amplitude ranges, and the stimulation threshold falls within the indicated range. The color-coded indicator may include at least three ranges, including at least one safe region and at least one unsafe region.

According to one aspect, a system for neuromonitoring includes a (1) surgical instrument for delivering stimulus signals to tissue including or adjacent to a nerve and (2) a processing system that includes (A) a detection module configured to detect, in muscle tissue, a first neuromuscular response in response to a first stimulus signal having a first amplitude and to detect a second neuromuscular response in response to a second stimulus signal having a second amplitude; (B) a processing module in communication with the detection module and configured to calculate a stimulation threshold for the nerve from the first and second stimulus signal amplitudes and the first and second neuromuscular responses, the stimulation threshold being an estimate of a minimum stimulus level required to elicit a neuromuscular response greater than or equal to a predetermined threshold; and (C) a communications module in communication with the processing module and configured to communicate an indicator of the stimulation threshold to a user to indicate at least one of nerve proximity and pedicle integrity.

In certain implementations, the surgical instrument includes a probe coupled to an electrical source, and a stimulating electrode may be disposed on a distal end of the probe. The detection module may include a sensing electrode configured to detect EMG signals, and the sensing electrode may include a surface EMG electrode or a needle EMG electrode. In certain implementations, the detection module is configured to detect neuromuscular responses in the muscle tissue during predetermined time windows, and the predetermined time windows may be offset from delivery times of the first and second stimulus signals. The predetermined time windows may be offset based on a signal transit time associated with the nerve and the muscle tissue.

In certain implementations, the processing module is configured to calculate a linear function from the first and second stimulus signal amplitudes and the first and second neuromuscular responses, and the processing module may be further configured to determine the threshold stimulation from the linear function. In other implementations, the processing module is configured to calculate a curve fit from the first and second stimulus signal amplitudes and the first and second neuromuscular responses, and the processing module may be further configured to determine the threshold stimulation from the curve fit. The curve fit may be a sigmoid function.

In certain implementations, the detection module is configured to apply a voltage level threshold to detected EMG signals. In other implementations, the detection module is configured to cross-correlate detected EMG signals with an EMG response template, and the detection module may be configured to apply a correlation level threshold to the cross-correlation.

In certain implementations, the processing system includes a control module configured to select the amplitudes of the first and second stimulus signals, and the control module may be configured to select the amplitudes from a curve fit of test stimulus signal amplitudes and test neuromuscular responses.

According to one aspect, a system for neuromonitoring includes (1) means for delivering stimulus signals to tissue including or adjacent to a nerve; (2) means for detecting, in muscle tissue, a first neuromuscular response in response to a first stimulus signal having a first amplitude; (3) means for detecting, in the muscle tissue, a second neuromuscular response in response to a second stimulus signal having a second amplitude; (4) means for calculating a stimulation threshold for the nerve from the first and second stimulus signal amplitudes and the first and second neuromuscular responses, the stimulation threshold being an estimate of a minimum stimulus level required to elicit a neuromuscular response greater than or equal to a predetermined threshold; and (5) means for communicating an indicator of the stimulation threshold to a user to indicate at least one of nerve proximity and pedicle integrity.

In certain implementations, the means for delivering stimulus signals includes a probe coupled to an electrical source means, and a stimulating means may be disposed on a distal end of the probe. In certain implementations, the means for detecting includes a means for sensing EMG signals, and the means for sensing may include a surface EMG electrode or a needle EMG electrode.

In certain implementations, the means for detecting includes means for detecting neuromuscular responses in the muscle tissue during predetermined time windows, and the predetermined time windows may be offset from delivery times of the first and second stimulus signals. The predetermined time windows may be offset based on a signal transit time associated with the nerve and the muscle tissue.

In certain implementations, the means for calculating includes means for calculating a linear function from the first and second stimulus signal amplitudes and the first and second neuromuscular responses, and the means for processing may include means for determining the threshold stimulation from the linear function. In other implementations, the means for calculating includes means for calculating a curve fit from the first and second stimulus signal amplitudes and the first and second neuromuscular responses, and the means for processing may include means for determining the threshold stimulation from the curve fit. The curve fit may be a sigmoid function.

In certain implementations, the means for detecting includes means for applying a voltage threshold to detected EMG signals. In other implementations, the means for detecting includes means for cross-correlating detected EMG signals with an EMG response template, and the means for detecting may include means for applying a correlation level threshold to the cross-correlation. In certain implementations, the system includes a means for selecting the amplitudes of the first and second stimulus signals, and the means for selecting may include means for selecting the amplitudes from a curve fit of test stimulus signal amplitudes and test neuromuscular responses.

According to one aspect, a method for neuromonitoring includes the steps of (1) delivering a first stimulus signal having a first pulse width and a second stimulus signal having a second pulse width to tissue including or adjacent to a nerve, the first pulse width being different from the second pulse width; (2) detecting, in muscle tissue, a first neuromuscular response in response to the first stimulus signal and a second neuromuscular response in response to the second stimulus signal; (3) determining a stimulation threshold for the nerve from the first and second pulse widths and the first and second neuromuscular responses, the stimulation threshold being an estimate of a minimum pulse width required to elicit a neuromuscular response greater than or equal to a predetermined threshold; and (4) communicating to a user an indicator of the stimulation threshold to indicate at least one of nerve proximity and pedicle integrity.

In certain embodiments, the first and second stimulus signals are delivered at a constant current, and the first and second stimulus signals may be delivered at a constant voltage.

In certain implementations, the method includes delivering a plurality of stimulus signals, each stimulus signal having a larger pulse width than a preceding stimulus signal. The pulse width of the stimulus signals in the plurality of stimulus signals may increase at a constant increment or may increase at varying increments. Delivering a plurality of stimulus signals may include delivering stimulus signals until a neuromuscular response greater than or equal to the predetermined threshold is detected. The second neuromuscular response may be the first detected neuromuscular response greater than or equal to the predetermined threshold, and communicating an indicator may include communicating the second pulse width to the user.

In certain implementations, the first and second pulse widths define an initial pulse width range, and determining a stimulation threshold includes delivering stimulus signals having pulse widths selected from within the initial pulse width range to determine a minimum pulse width required to elicit a neuromuscular response greater than or equal to the predetermined threshold. Delivering stimulus signals having pulse widths selected from within the initial pulse width range may include delivering a sequence of stimulus signals having pulse widths that either increase by a constant increment or decrease by a constant decrement. In certain implementations, the sequence of stimulus signals is delivered from a first stimulus signal near a lower bound of the initial pulse width range and increasing the pulse width of subsequent stimulus signals to a value near an upper bound of the initial pulse width range. In other implementations, the sequence of stimulus signals is delivered from a first stimulus signal near an upper bound of the initial pulse width range and decreasing the pulse width of subsequent stimulus signals to a value near a lower bound of the initial pulse width range. In certain implementations, a subsequent stimulus pulse is delivered having a pulse width equal to a midpoint of the initial pulse width range.

In certain implementations, communicating an indicator includes displaying an indication of electric charge, and the indication of electric charge may be displayed in coulombs. In other implementations, communicating an indicator includes displaying a distance between the nerve and a surgical instrument, and the method may include calculating the displayed distance from an electric charge corresponding to the stimulation threshold. In other implementations, communicating an indicator includes displaying a pulse width corresponding to the stimulation threshold. The method may also include communicating at least one of a constant current or constant voltage at which the first and second stimulus signals are delivered.

In certain implementations, the first neuromuscular response is detected before the second stimulus signal is delivered. In other implementations, the second stimulus pulse is delivered before the first neuromuscular response is detected, and an offset time between delivery of the first stimulus pulse and delivery of the second stimulus pulse may be greater than or equal to a refractory period associated with the nerve and the muscle tissue.

According to one aspect, a system for neuromonitoring includes (1) a surgical instrument for delivering stimulus signals to tissue including or adjacent to a nerve and a processing system including (A) a detection module configured to detect, in muscle tissue, a first neuromuscular response to a first stimulus signal having a first pulse width and to detect a second neuromuscular response to a second stimulus signal having a second pulse width; (B) a processing module in communication with the detection module and configured to determine a stimulation threshold for the nerve from the first and second stimulus signal pulse widths and the first and second neuromuscular responses, the stimulation threshold being an estimate of a minimum pulse width required to elicit a neuromuscular response greater than or equal to a predetermined threshold; and (C) a communications module in communication with the processing module and configured to communicate an indicator of the stimulation threshold to indicate at least one of nerve proximity and pedicle integrity.

In certain implementations, the surgical instrument includes a probe coupled to an electrical source, and a stimulating electrode may be disposed on a distal end of the probe. In certain implementations, the detection module includes a sensing electrode configured to detect EMG signals, and the sensing electrode may be a surface EMG electrode or a needle EMG electrode. In certain implementations, the detection module is configured to detect neuromuscular responses in the muscle tissue during predetermined time windows, and the predetermined time windows may be offset from delivery times of the first and second stimulus signals. The predetermined time windows may be offset based on a signal transit time associated with the nerve and the muscle tissue.

In certain implementations, the processing system includes a control module configured to deliver a plurality of stimulus signals, each stimulus signal having a larger pulse width than a preceding stimulus signal. The control module may be configured to increase the pulse width of the stimulus signals in the plurality of stimulus signals at a constant increment or at varying increments.

In certain implementations, the detection module is configured to apply a voltage level threshold to detected EMG signals. In other implementations, the detection module is configured to cross-correlate detected EMG signals with an EMG response template, and the detection module may be configured to apply a correlation level threshold to the cross-correlation.

In certain implementations, the communications module includes a display configured to display an indication of electric charge, and the indication of electric charge may be displayed in coulombs. In other implementations, the communications module includes a display configured to display a distance between the nerve and the surgical instrument, and the processing module may be configured to calculate the displayed distance from the stimulation threshold. In other implementations, the communications module includes a display configured to display a pulse width corresponding to the stimulation threshold. In certain implementations, the communications module is further configured to communicate at least one of a constant current or a constant voltage at which the first and second stimulus signals are delivered.

According to one aspect, a neuromonitoring system includes (1) means for delivering stimulus signals to tissue including or adjacent to a nerve; (2) means for detecting, in muscle tissue, a first neuromuscular response to a first stimulus signal having a first pulse width; (3) means for detecting, in muscle tissue, a second neuromuscular response to a second stimulus signal having a second pulse width; (4) means for determining a stimulation threshold for the nerve from the first and second stimulus signal pulse widths and the first and second neuromuscular responses, the stimulation threshold being an estimate of a minimum pulse width required to elicit a neuromuscular response greater than or equal to a predetermined threshold; and (5) means for communicating an indicator of the stimulation threshold to indicate at least one of nerve proximity and pedicle integrity.

In certain implementations, the means for delivering stimulus signals includes a probe coupled to an electrical source means, and a stimulating means may be disposed on a distal end of the probe. In certain implementations, the means for detecting includes a means for sensing EMG signals, and the means for sensing may include a surface EMG electrode or a needle EMG electrode.

In certain implementations, the means for detecting includes a means for detecting neuromuscular responses in the muscle tissue during predetermined time windows, and the predetermined time windows are offset from delivery times of the first and second stimulus signals. The predetermined time windows may be offset based on a signal transit time associated with the nerve and the muscle tissue.

In certain implementations, the means for determining includes a control means for delivering a plurality of stimulus signals, each stimulus signal having a larger pulse width than a preceding stimulus signal. The control means may include means for increasing the pulse width of the stimulus signals in the plurality of stimulus signals at a constant increment or at varying increments.

In certain implementations, the means for detecting includes means for applying a voltage level threshold to detected EMG signals. In other implementations, the means for detecting includes means for cross-correlating detected EMG signals with an EMG response template, and the means for detecting may include means for applying a correlation level threshold to the cross-correlation.

In certain implementations, the means for communicating includes means for displaying an indication of electric charge, and the indication of electric charge may be displayed in coulombs. In other implementations, the means for communicating includes means for displaying a distance between the nerve and the means for delivering stimulus signals, and the means for processing may include means for calculating the displayed distance from the stimulation threshold. In other implementations, the means for communicating includes means for displaying a pulse width corresponding to the stimulation threshold. In certain implementations, the means for communicating includes means for communicating at least one of a constant current or a constant voltage at which the first and second stimulus signals are delivered.

According to one aspect, a system for neuromonitoring includes (1) a surgical accessory having at least one stimulation electrode; (2) a processing system configured to (A) stimulate the at least one stimulation electrode with an electrical stimulation signal having pulses, (B) measure a neuromuscular response caused by nerves depolarized by the stimulation signal, and (C) automatically determine a stimulation threshold of the nerves by automatically adjusting a pulse width of the stimulation signal; and (3) a communication module configured to communicate to a user an indication of the stimulation threshold to indicate at least one of nerve proximity and pedicle integrity.

In certain implementations, the processing system is configured to automatically adjust the pulse width by variable amounts, while in other implementations the processing system is configured to automatically adjust the pulse width by constant amounts. In certain implementations, the processing system is configured to maintain the stimulation signal at a fixed current amplitude, while in other implementations the processing system is configured to vary an amplitude of the stimulation signal by either variable or constant amounts.

In certain implementations, the processing system is configured with a plurality of predetermined ranges and the communication module is configured to communicate to the user by indicating which one of the predetermined ranges the stimulation threshold falls within. The plurality of predetermined ranges may include ranges of pulse widths, or the plurality of predetermined ranges may include ranges of coulombs indicating the total charge delivered by the stimulation electrode.

In certain implementations, the communication module is configured to communicate to the user by displaying information on at least first and second display screens. The communication module may be configured to display the indicator on the first display screen and an EMG waveform corresponding to the measurement on the second display screen.

In certain implementations, the processing system is configured to automatically determine the stimulation threshold by calculating the stimulation threshold from a plurality of stimulation pulses having variable pulse width and measured responses corresponding to the plurality of stimulation pulses.

According to one aspect, a method for neuromonitoring includes the steps of (1) delivering by a stimulating electrode located on a surgical accessory a plurality of stimulation signals to tissue including or adjacent to a nerve; (2) detecting by a sensor associated with muscle tissue associated with the nerve a plurality of neuromuscular responses elicited by the stimulation signals; (3) calculating a stimulation threshold for the nerve by extrapolation from the neuromuscular responses; and (4) communicating an indicator of the stimulation threshold to a user to indicate one of nerve proximity and pedicle integrity.

Variations and modifications of these embodiments will occur to those of skill in the art after reviewing this disclosure. The foregoing features and aspects may be implemented, in any combination and subcombination (including multiple dependent combinations and subcombinations), with one or more other features described herein. The various features described or illustrated herein, including any components thereof, may be combined or integrated in other systems. Moreover, certain features may be omitted or not implemented.

BRIEF DESCRIPTION OF THE DRAWINGS

The foregoing and other objects and advantages will be apparent upon consideration of the following detailed description, taken in conjunction with the accompanying drawings, in which like reference characters refer to like parts throughout.

FIGS. 15-19 depict illustrative sequences of stimulus signals and corresponding detected EMG responses.

FIGS. 27-30 depict various illustrative dials displayed during a surgical procedure.

DETAILED DESCRIPTION

Figure 1:
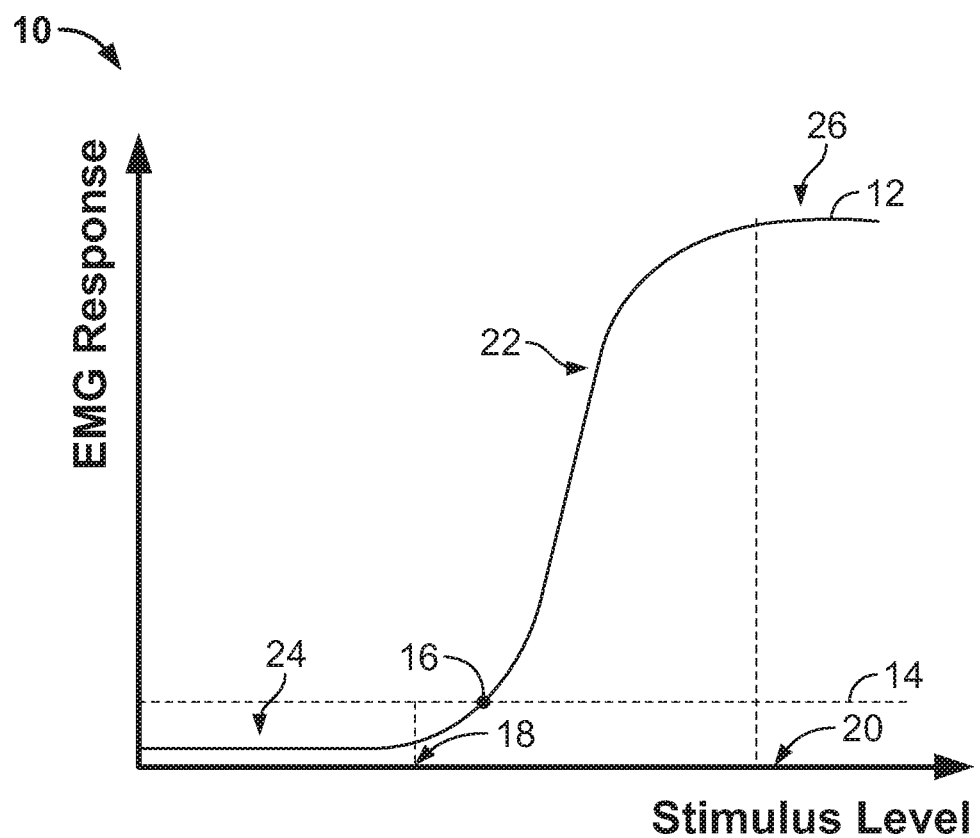
FIG. 1 depicts an illustrative trend of EMG responses.

To provide an overall understanding of the systems, devices, and methods described herein, certain illustrative embodiments will be described. Although the embodiments and features described herein are specifically described for use in connection with spinal surgical procedures, it will be understood that the system components, connection mechanisms, surgical procedures, and other features outlined below may be combined with one another in any suitable manner and may be adapted and applied to systems to be used in other surgical procedures performed in the proximity of neural structures where nerve avoidance, detection, or mapping is desired, including, but not limited to spine surgeries, brain surgeries, carotid endarterectomy, otolaryngology procedures such as acoustic neuroma resection, parotidectomy, nerve surgery, or any other suitable surgical procedures.

The present disclosure relates to systems, devices, and methods for intraoperative neuromonitoring (IONM) of any of evoked potential (EP), transcranial electrical motor evoked potential (TceMEP), electromyography (EMG), and electroencephalogram (EEG) signals. Intraoperative neuromonitoring reduces the risk of permanent injury to neural structures during surgical procedures. Changes or abnormalities in the recorded signals may indicate that the surgical procedure is affecting the neural structure. The systems, devices, and methods of the present disclosure measure and display the electrical signals generated by any of muscles, the central nervous system, and peripheral nerves and acquire the data necessary to perform intraoperative monitoring of neural pathways to prevent damage to neural structures during surgical procedures. It will be appreciated that the systems, devices, and methods of the present disclosure can be adapted for use in pre- and post-operative procedures in addition to or in place of intraoperative procedures.

Electrical nerve assessment can be employed during a lateral approach spinal surgery in which instruments are advanced to the spine in a trans-psoas approach through a user's side. Such an approach may be preferred to gain access to the spine, for example to vertebral pedicles, and to provide advantageous angles for insertion of pedicle screws. Instruments approaching the spine laterally must be advanced with caution, as sensitive nerve roots from the spinal cord exit the spine in lateral directions, and harm or unintentional stimulation of these nerve roots can cause pain or damage. In order to avoid unwanted contact with these nerves, electrical assessment procedures discussed herein may be used to determine the proximity of nerves and warn a surgeon if an instrument is approaching too near to one or more of the nerve roots. By applying stimulus currents to the instruments and measuring the responses in muscles innervated by the nerve roots, such processes can guide a surgeon through the lateral muscles and to the spine without unintentionally contacting or damaging the nerves.

These electrical nerve assessment processes may also be used to evaluate and monitor the integrity of a pedicle during tapping, insertion, and final placement of a spinal screw once instruments are advanced to the spine. The pedicles of a vertebra form the medial and lateral boundaries of the canal through the spine that houses the spinal cord, and lateral nerve roots extend outward from the spinal cord near the pedicles. Any screw or other instrument advanced into the pedicle is, preferably, precisely inserted so as to avoid compromising the walls of the pedicle and exposing the screw or instrument to the sensitive nerve tissue. In order to evaluate the integrity of a pedicle during these sensitive processes, an electrical stimulus and muscle monitoring approach such as the approaches discussed herein may be employed. The bone material that forms the pedicle insulates an interior channel through the pedicle, and instruments placed into the channel, from the sensitive surrounding nerves. Thus, an uncompromised pedicle will prevent surrounding nerves from becoming stimulated by an electrical stimulus applied to the interior channel. However, if the pedicle walls are compromised or nearly compromised during drilling or placement of an instrument, the insulation may be compromised and may result in surrounding nerves being stimulated from an internal stimulus pulse. During or after tapping the pedicle and placing a screw, the electrical assessment procedures discussed herein may be used to apply stimulus to a pedicle or to a screw placed in the pedicle, and responses of muscles innervated by local nerves can be used to identify damaged or compromised pedicles.

Electrical stimulus applied to a patient's tissue should be applied carefully. Application of too much current can cause damage to tissue and to nerves within the tissue, and can cause pain to the patient. However, multiple test stimulations may be needed to accurately detect and assess the proximity or location of nerves within the tissue being stimulated. This establishes a trade-off between delivering enough stimulation and detecting enough muscle responses to that stimulation in order to accurately provide a surgeon with precise information on nerve proximity and limiting the number of stimulations delivered in order to avoid causing unnecessary harm to a patient. If too few stimulations are used, the data provided to a surgeon may not be entirely accurate, and may lead to mistakes made during surgery due to inadequate nerve proximity information. On the other hand, if too many stimulations are delivered, the overall amount of current and electrical energy delivered to the patient's tissue may cause unwanted side effects. This trade-off may be managed by utilizing an estimation technique that allows adequate information to be calculated for providing to a surgeon while still limiting or decreasing the number of stimulations required to obtain that information.

FIG. 1 depicts a graph 10 showing a standard neuromuscular EMG response profile of a muscle innervated by a nerve near the source of a delivered stimulus signal. As shown in the trend 12 in the graph 10, the magnitude of an EMG response sensed at the muscle tissue increases as the stimulus signal level increases near a nerve that innervates the monitored muscle. The increase in stimulus signal level may be the result of adjusting one or more of current voltage, charge, or pulse width of a delivered stimulus. When the delivered stimulus signal is small, for example, when the stimulus signal is delivered at a low current or low voltage, an EMG electrode picks up little or no EMG response, as shown in a first portion 24 of the trend 12. When the stimulus signal is increased to a level that begins to activate innervated muscle, for example, after level stimulus 18 in the graph 10, the muscle begins to respond and contract, and an increased EMG response is picked up by the electrode. As the stimulus signal level continues to increase, this muscle response increases as shown by the middle portion 22 of the trend 12, denoting a zone where one or more muscles is actively contracting because of the applied stimulation. The monitored muscle has a maximum response level, for example a maximum possible contraction and EMG activity at approximately amplitude 20 in graph 10. As the stimulus increases beyond level 20, the innervated muscle reaches the maximum response and begins to plateau, as seen in the third portion 26 of the trend 12. Also shown in FIG. 1 is point 16 on the curve 10. Point 16 represents a point where the EMG response trend 12 transitions from the unresponsive portion 24 to the actively contracting zone 22, or the transition from sub-threshold to above threshold EMG activity. This transition point is often sought during neuromonitoring. For example, to determine the distance from a probe to a nerve or to evaluate the integrity of a bone structure, it is often desirable to locate the stimulus level at or near the point where the EMG response trend 12 transitions from portion 24 to portion 22. The stimulus at this transition indicates the minimum stimulus level needed to elicit a measurable response from the nerve and the innervated muscle. In order to differentiate EMG signals from noise and determine the threshold stimulus, an EMG threshold, such as threshold 14, can be applied to the EMG response profile in order to determine the stimulus signal level at which the trend 12 crosses the threshold 14. Various methods discussed below can be applied to determine or nearly estimate the stimulus required to reach point 16 and its corresponding EMG muscle response. In order to locate various points along the trend 12 for a given nerve and innervated muscle, a neuromonitoring system can deliver a variety of stimulus pulses at different levels and monitor responses from the muscle in order to analyze the health, proximity, or other characteristic of the nerve.

Figure 2:
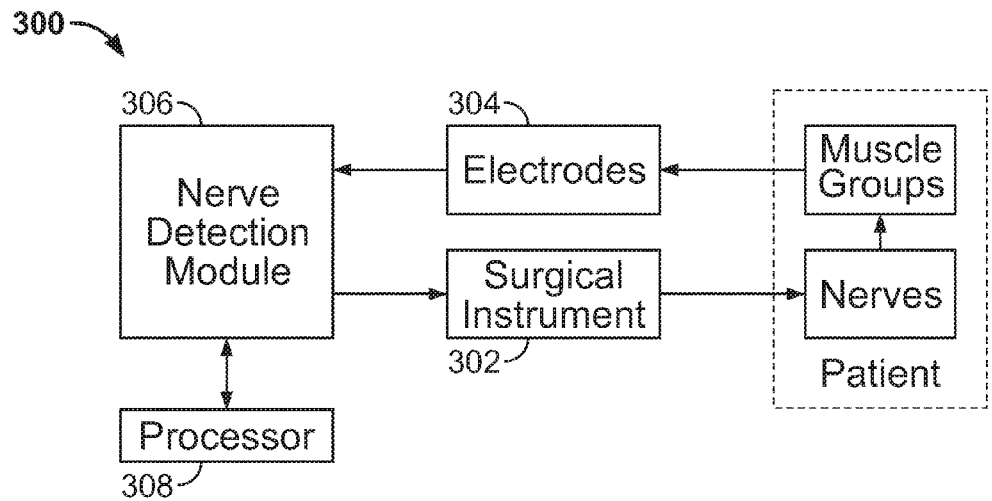
FIG. 2 depicts an illustrative surgical monitoring system coupled to a surgical instrument and electrode.

FIG. 2 shows components of a surgical neuromonitoring system according to certain embodiments. The surgical monitoring system 300 includes a surgical instrument 302 for delivering stimulation pulses. The stimulating may be accomplished by applying any of a variety of suitable stimulus signals to an electrode or electrodes on the surgical instrument, including voltage and/or current pulses of varying magnitude and/or frequency. Any suitable surgical instruments may be employed, including, but not limited to, any number of devices or components for creating an operative corridor to a surgical target site (such as K-wires, sequentially dilating cannula systems, distractor systems, and/or retractor systems), devices or components for assessing pedicle integrity (such as a pedicle testing probe), and/or devices or components for retracting or otherwise protecting a nerve root before, during and/or after surgery (such as a nerve root retractor).

Measuring the response of nerves to the stimulation pulses may be performed in any suitable manner, including but not limited to the use of compound muscle action potential (CMAP) monitoring techniques using electrodes 304 coupled to a patient (e.g., measuring the EMG responses of muscle groups associated with a particular nerve). In certain embodiments, measuring the response of nerves is accomplished by monitoring or measuring the EMG responses of the muscles innervated by the stimulated nerves. The nerve detection module 306 and/or the processor 308 may digitize the signals and split the signal into components communicated to a display instrument to provide a surgeon or other user with a visual display of the detected data.

Figure 3:
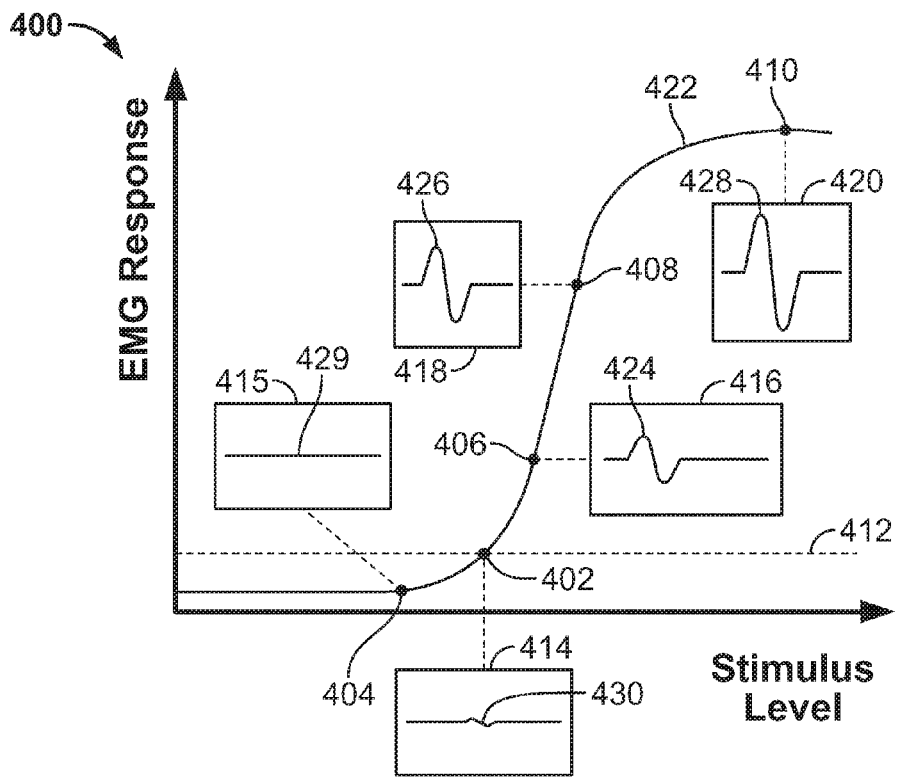
FIG. 3 depicts illustrative detected EMG responses for multiple stimulus signals.

A neuromonitoring system such as the system 300 shown in FIG. 2 delivers a plurality of stimulus signals, senses muscle responses to the stimulus, and processes the detected responses in order to identify EMG responses, for example using the threshold determinations discussed below. This neuromonitoring process uses detection and processing of EMG responses that are similar to typical EMG responses to stimulus signals that lie along the known response trend shown in FIG. 1. For example, the magnitude of an EMG response detected during surgery can be used to locate the response long the typical trend in FIG. 1 and then assess the stimulated nerve based on the location of the response in the trend. FIG. 3 shows a graph 400 that depicts some illustrative EMG voltage responses along the trend shown in FIG. 1 that may be elicited and detected by a neuromonitoring system, such as the system 300. The trend 422 in graph 400 shows the typical EMG response trend over a range of stimulus levels. On the trend 422 are five stimulation points 402, 404, 406, 408 and 410, along with their respective detected EMG responses 414, 415, 416, 418 and 420. The responses 414, 415, 416, 418, and 420 may be sensed, for example, by an EMG electrode, such as the electrode shown in FIG. 2, when the respective stimulus signals are delivered. The EMG response at point 404 falls below a threshold 412 along the trend 422, while the EMG response at points 402, 406, 408 and 410 on/or fall above the threshold 412. The EMG responses shown in windows 414, 415, 416, 418 and 420 illustrate the corresponding change in the magnitudes of detected EMG responses as stimulus level is increased, and the responses pass the EMG response threshold 412.

Starting below the threshold 412, when the stimulus is delivered at point 404, little or no EMG response is sensed by an electrode. As shown in window 415, there is no movement from the baseline of the sensed EMG signal 429. The response processing employed detects little or no movement from baseline in the signal 429, and indicates that the stimulus signal did not elicit an EMG response above the threshold 412. The next stimulation at point 402 falls right on the threshold 412, and the corresponding response 430 in window 414 shows a small EMG response. The response 430 is a deviation having a standard EMG shape, with a low response magnitude. Because point 402 lies on threshold 412, the processing system recognizes the peak 430 as a threshold EMG response. After the next stimulus at point 406, the response shown in window 416 again has an appreciable deviation from baseline in a peak 424 detected by an electrode. The peak 424 is a significant deviation from the baseline, and follows the standard trend of an EMG signal. Post-processing of the signal in window 416 processes the peak 424 and identifies the point 406 as a stimulus and EMG response falling above the cut-off threshold 412. As the stimulus level is increased to point 408, the corresponding detected EMG response in window 418 also increases. The response in window 418 exhibits a peak 426 deviating from the baseline EMG detection. The peak 426 has a sharper incline and a higher peak deviation than the peak 424 detected at point 406. The higher peak 426 shown in window 418 is the result of a greater EMG response elicited from the monitored muscle by the stimulus delivered at point 408. Continuing further along the trend 422, the stimulus delivered at point 410 elicits an even greater EMG response, shown by the peak 428 in window 420. The peak 428 indicates an EMG response shown as a deviation from baseline typical of an EMG response, as the shape of the wave in window 420 mimics the waves shown in windows 416 and 418. The peak 428 has a higher deviation from baseline than both the peaks 426 and 424 as a result of the EMG response elicited by the greater stimulus level at point 410. Point 410 is located in the plateau region of the trend 422, and thus further increases in the stimulus level, not shown in the graph 400, would be expected to elicit similar responses as the response shown in window 420.

The EMG responses illustrated in windows 414, 415, 416, 418 and 420 in FIG. 3 show the difference between EMG responses below the threshold 412 and at/or above the threshold level. In order to determine the precise location of the stimulation threshold 402, many conventional systems apply techniques that require using multiple stimulations to locate a narrow estimate of the location of point 402. Not only can these approaches take a long time to converge on the accurate location (and thus provide feedback to the surgeon), they may endanger patient safety by application of unnecessary stimulation signals. In addition, such conventional systems are limited in their precision because the threshold stimulation is necessarily a value at which an actual stimulation signal was applied. That is, conventional systems do not display a calculated value as the stimulation threshold, but rather require that the displayed stimulation threshold correspond to a value applied to tissue within the patient. Thus, to provide a precision within 0.1 mA, for example, such conventional systems employ stimulation signals at currents that are adjusted by increments of 0.1 mA until the threshold is determined. According to an aspect of neuromonitoring device and methods described herein, the EMG response and associated stimulus level that correspond to the threshold point 402 are estimated from other stimulation and response information in the graph. In particular, in order to accurately estimate or determine the stimulus level corresponding to the point 402, a neuromonitoring system processes one or more of the EMG responses detected at other points in the trend 422 that do not, preferably, correspond to the threshold itself. When a stimulus is delivered and an EMG response is detected, a standard post-processing system is applied to analyze the detected signal to determine where along the trend 422 the delivered stimulus point lies. In one implementation, the post-processing system determines first if there is an appreciable EMG signal, and second determines the magnitude of the detected EMG response to determine where along the trend 422 the stimulus point lies.

Figure 4:
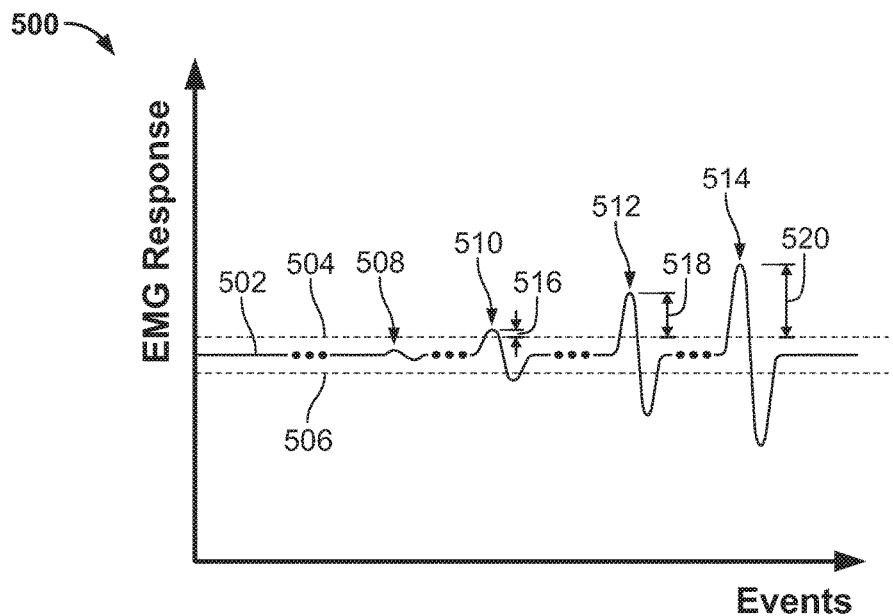
FIG. 4 depicts an illustrative amplitude threshold applied to detected EMG signals.

In some implementations, this is done by applying a straight voltage threshold to detected EMG signals in order to identify and evaluate the magnitude of potential EMG responses. Graph 500 shown in FIG. 4 depicts two such thresholds applied to a detected EMG signal 502—an upper EMG response threshold 504 and a lower EMG response threshold 506. Those two thresholds can be selected by the operator or surgeon to set a preferred level of EMG sensitivity for the EMG detection module, or the thresholds may be standard thresholds set by the detection system. Also shown, the detected signal 502 includes four peaks 508, 510, 512 and 514, which may or may not be actual EMG responses to delivered stimulus signals. In the graph 500, the thresholds 504 and 506 are applied to each of the potential EMG peaks in order to determine both whether the peak is an actual EMG response or an artifact and also to evaluate the magnitude of the EMG response when an actual response is detected. At each peak, the system compares the EMG signal to the positive magnitude threshold 504 and the negative magnitude threshold 506 and determines whether one or both of the thresholds has been exceeded. If neither threshold is exceeded, the potential response is determined to be either too small to be an appreciable EMG response or is determined to be artifact in the signal 502 caused, for example, by noise in the detection system. Thus, the peak 508 is judged to be either an insignificant EMG response or noise, as the peak 508 does not cross the threshold 504 or the threshold 506. At peaks 510, 512 and 514, however, the signal 502 does exceed the threshold 504 and the threshold 506, and these three peaks are judged as significant EMG responses. For example, referring back to graph 400 in FIG. 3, the peak 508 may be judged as an EMG response at point 404, falling below the threshold 412 in graph 400, while the peaks 510, 512 and 514 may be EMG responses elicited by stimulus signals at points 406, 408 and 410 respectively, above the threshold 412 in graph 400.

In addition to determining whether or not the peaks in the signal 502 are significant EMG responses, the neuromonitoring system processes each detected response to determine where along the typical EMG response trend, for example trend 422 in graph 400, each EMG response lies. This determination may be performed, for example, by determining the degree to which each peak surpasses one of the thresholds 504 and 506. In FIG. 4, the peaks 510, 512 and 514 each surpass the upper threshold 504 by increasing amounts shown by offsets 516, 518 and 520, respectively. The offset 516 of the peak 510 from the threshold 504 is a relatively small offset and indicates that the peak 510, as well as its corresponding stimulus level, likely lies near the threshold in a typical EMG response trend, for example the trend shown in FIG. 1. The higher offset 518 of peak 512 and the higher offset 520 of peak 514 indicate that the stimulus level corresponding to those two peaks lie further along the typical EMG response trend. Using this information, a processing system can take the four peaks 508, 510, 512 and 514, and their corresponding stimulus levels, and estimate where along a typical EMG response each peak and stimulus lies. The corresponding positions of the stimulus levels that elicit the peaks can then be used in a determination or modeling estimation approach to determine the minimum stimulus level that is required to produce an EMG response in signal 502 that peaks right at one of the thresholds 504 and 506.

An EMG signal threshold such as that depicted in graph 500 may be sufficient for identifying when EMG responses are present in detected EMG signals, but such approaches may also be vulnerable to inaccuracies or false positives due to signal noise. For example, if a noise interruption is great enough, it may cause the baseline EMG signal to quickly jump either above an upper threshold or below a lower threshold, thus triggering a threshold detector to indicate an EMG response. While the EMG signal may exceed one of the thresholds, the shape and pattern of the signal may make it quite clear that the detected increase or decrease from the baseline is simply noise and not an actual EMG response to a stimulus pulse. In the case of manual EMG review, a physician would recognize that the quick sharp peaks caused by signal noise do not look like an EMG response, and a physician viewing the signals can dismiss such a signal as an insignificant deviation. The straight threshold detector, however, is not capable of making this comparison, and incorporating a check or an alternate trigger that is based on the shape and orientation of the EMG signal may produce better EMG response detection.

Figure 5:
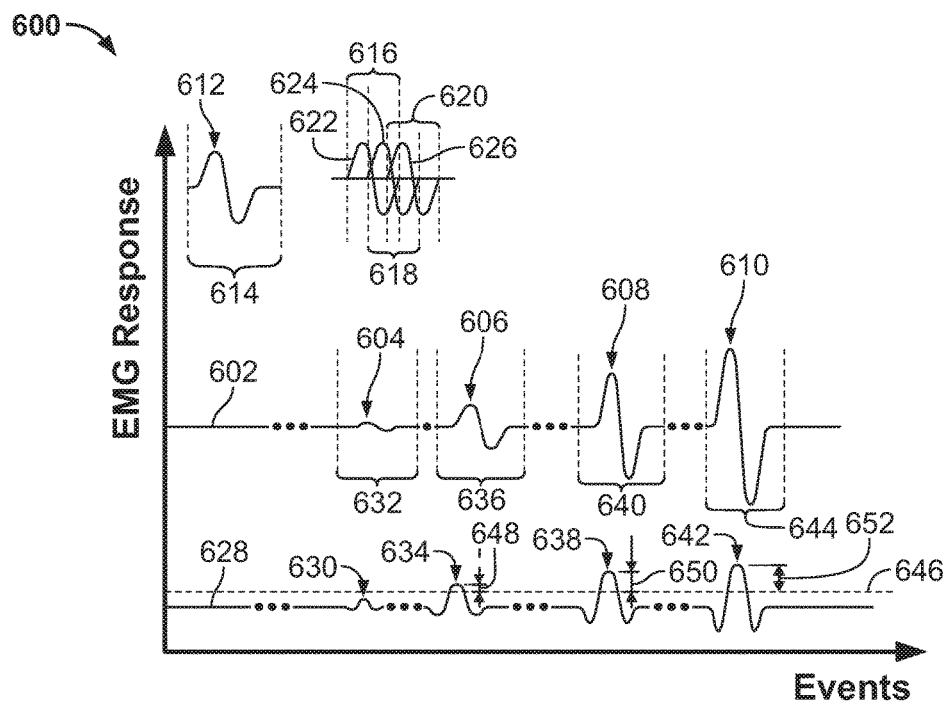
FIG. 5 depicts an illustrative cross-correlation of detected EMG signals and an illustrative threshold of applied to the cross-correlation.

FIG. 5 shows an illustrative graph 600 that depicts a correlation approach that uses the shape and pattern of a typical EMG response to improve EMG detection and processing detected signals, thus providing a more robust detection mechanism. It is understood that while the correlation approach described below may reduce susceptibility to noise and thus improve the reliability of the overall detection, the straight threshold detector discussed above may be used where the signal-to-noise ratio is sufficiently low. Therefore, the methods and system disclosed herein are not limited to use of a correlation-based detector. Shown in the graph 600 is a detected EMG signal 602 and a correlation signal 628 produced by processing the EMG signal 602. In order to produce the correlation signal 628, the EMG signal 602 is processed by comparing portions of the signal 602 to a template 612 that is indicative of a typical size and shape of an EMG response. The template 612 shows an EMG signal over a time window 614 that exhibits the expected EMG response profile from a muscle in which a contraction is triggered by a stimulus signal. In order to determine when EMG responses are present in the detected signal 602, the template 612 is frequently, or continuously, compared to portions of the signal 602 to identify patterns in the signal that match or closely mimic the template 612. A correlation function programmed into the processor compares the template 612 and the EMG signal 602. The correlation function shifts the template 612 to multiple points along the time axis of the EMG signal 602 and performs a mathematical calculation that compares the similarity of the template 612 and the signal 602 over several pre-selected time windows along the graph. For example, three template peaks 622, 624 and 626 are shown over three time windows 616, 618 and 620 respectively. At each of these time windows 616, 618 and 620, the correlation algorithm compares the shape and magnitude of the corresponding template peak 622, 624 and 626 to a corresponding time window portion of the EMG signal 602. The output of the correlation function is a number that indicates the similarity between the respective template and the EMG signal 602 at a given time window.

The correlation signal 628 shows the results of comparing the template 612 to the EMG signal 602 in a continuous manner along the time domain of EMG signal 602. The EMG signal 602 includes four peaks 604, 606, 608 and 610 that may or may not be elicited EMG responses detected by an EMG electrode. As the template 612 is shifted across the EMG signal 602, the similarity between the template 612 and each of the peaks 604, 606, 608 and 610 results in corresponding peaks 630, 634, 638 and 642 in the correlation signal 628. Each of the correlation peaks 630, 634, 638 and 642 indicates a period of similarity between the template 612 and the EMG signal 602. For example, the small correlation peak 630 corresponds to the similarity between the template 612 and the EMG signal 602 over the time window 632, which is equal to the time window 614 of the template 612. Likewise, each of the peaks 634, 638 and 642 correspond to the similarity between the magnitude and trends of EMG signal 602 and the template 612 detected over each of the time windows 636, 640 and 644, respectively.

While each of the EMG signal peaks 604, 606, 608 and 610 bears some similarity to the template peak 612, not all the EMG signal peaks are actual EMG responses. For example, while the peak 604 is a deviation from the baseline of the EMG signal 602, it is only a minor deviation and does not have the pronounced shape and features of the template 612. Thus, the correlation peak 630 detected at the EMG signal peak 604 is minor, while the later peaks 634, 638 and 642 are more pronounced, as their corresponding EMG peaks 606, 608 and 610 more closely mimic the shape and size of the EMG template 612. In order to differentiate the deviations in EMG signal 602 that represent actual EMG responses and those which are noise or minor deviations, a threshold 646 is applied to the correlation signal 628.

The true neuromuscular responses in the EMG signal 602 are detected by identifying the points at which the correlation signal 628 exceeds the threshold 646. Similar to the EMG voltage threshold shown in graph 500, a deviation of the correlation 628 beyond the threshold 646 indicates a feature in the EMG signal 602 that should be considered a legitimate EMG response. As with the EMG threshold, the degree to which each identified peak exceeds the threshold 646 can be used as an indicator of the location along the typical EMG response curve that each peak falls. For example, each of peaks 634, 638 and 642 exceeds the threshold 646, but the three peaks exceed the threshold by differing degrees, increasing from offset 648 for peak 634 to offset 650 for peak 638 and offset 652 for peak 642. Using these correlation peaks and their offsets above the threshold 646, the processing system may place each of the EMG peaks 606, 608 and 610, and the corresponding stimulus levels that elicited each of the peaks, along the typical EMG response curve in order to calculate linear functions or other curve-fitting models for determining the minimum stimulus level required to elicit an EMG response. That is, the processor determines the minimum level required to produce a signal in the EMG signal 602 that leads to a correlation peak in the correlation signal 628 that rises just to the level of the threshold 646.

This is done, for example, by applying a voltage threshold or correlating the EMG signal, and processing the signals and responses to locate or estimate a minimum stimulus threshold. By relating detected EMG responses to a typical EMG response profile, for example the EMG trend shown in FIG. 1, the neuromonitoring system can reduce the number of stimuli and responses, and thus the time required, to locate the threshold within an acceptable resolution. Rather than continuously applying varied stimulus until a very narrow range of stimuli is determined within which the threshold lies, the standard trend profile can be applied to estimate the threshold stimulus level within an acceptable degree of accuracy. In some implementations, the trend profile is determined by performing an initial test on the patient, or the trend profile may be empirically determined.

Figure 6:
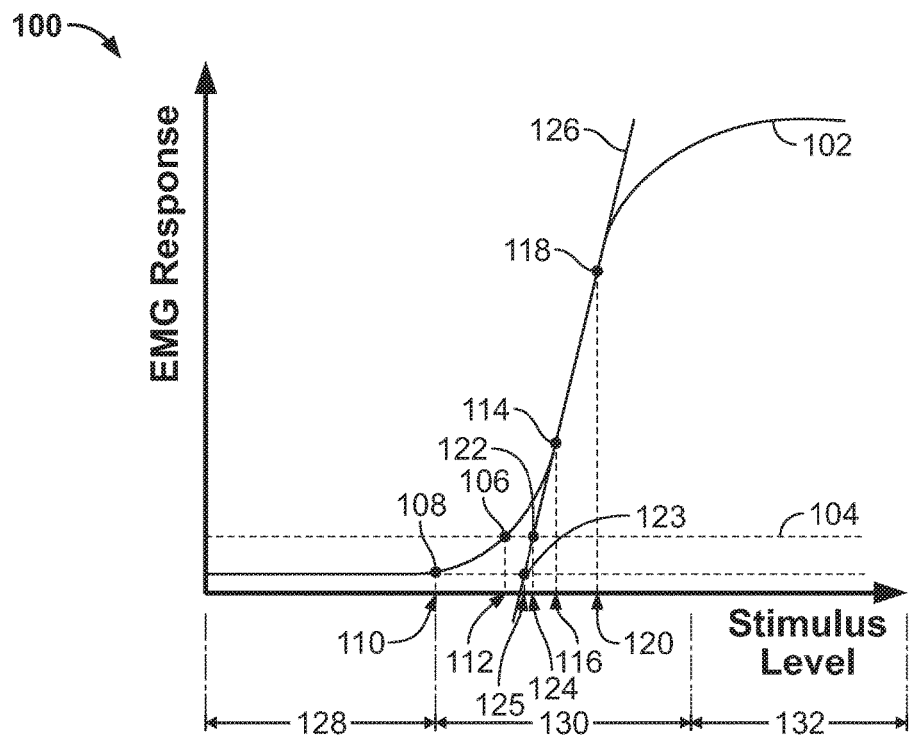
FIGS. 6-8 depict illustrative estimations of a threshold stimulation using linear modeling.

FIG. 6 depicts an illustrative approach for delivering stimulus pulses and calculating an estimated minimum threshold stimulus level based on neuromuscular responses elicited by the delivered stimulus pulses. The calculated threshold stimulation may be determined and communicated as a current, voltage, pulse width, charge or any other suitable stimulus level measurement. Graph 100 in FIG. 6 shows trend 102 in neuromuscular responses, for example voltages measured by EMG electrodes placed in or over muscle tissue, versus the level of stimulus signals, for example the current, voltage, pulse width, or charge delivered from a stimulus source. Trend 102 follows the typical shape of EMG response in a muscle innervated by a particular nerve when stimulus signals of increasing current are delivered to an area proximal that nerve. As shown, the trend 102 includes three portions: a first portion 128 over a range of stimulus levels that do not elicit any appreciable or detectable response from the muscle tissue; a second portion 130 over which an increasing EMG response is seen to the increasing stimulus levels; and a third portion 132 during which the EMG response levels off into a plateau over increasing stimulus levels. When a threshold level of EMG response, such as threshold 104, is applied to the trend 102, the point 106 may be used for a nerve proximity calculation. Alternatively, the point 108 at the transition between portions 128 and 130 may be used.

In order to accurately estimate the stimulation threshold 112 corresponding to point 106 or stimulus level 110 corresponding to point 108, multiple stimulus signals and corresponding EMG responses may be delivered and measured in order to locate a stimulus that produces an EMG response at or near the threshold point 106 or transition point 108 of the trend 102. This approach, however, may require delivering a large number of stimuli to a patient. In order to improve the efficiency of the threshold detection system and to improve patient safety, fewer stimulations may be delivered, and the estimation shown in FIG. 6 can be applied to estimate a point that is adequately close to the point 106 or point 108 for neuromonitoring purposes. In the example shown in graph 100, no stimulation is actually delivered at stimulus levels 110 or 112. Rather, two stimulations, at levels 116 and 120, are delivered to a patient, and EMG responses are detected corresponding to each stimulation signal. The detected EMG at point 114 for stimulus 116 and at point 118 for stimulus 120 provide enough data for the processing system to estimate the desired stimulation threshold. In certain implementations, the system may use the threshold 104 to estimate point 122 and stimulus level 124 as the threshold. In other implementations, the system may use the zero level of the EMG in portion 128 to estimate point 123 and stimulus level 125 as the threshold. The point 122 or 123 may coincide precisely with the minimum threshold value 106 or transition point 108, thereby providing the precise minimum stimulus that corresponds to the stimulation threshold. However, such precision may not be necessary in all applications. Thus, in some implementations, the estimated threshold stimulation level 124 provided by point 122 or 125 provided by point 123 is a short distance from the actual threshold 112 and may be sufficiently accurate information to avoid nerve injury. In some implementations, a confirmatory electrical stimulation signal may be delivered at the calculated threshold in order to confirm the calculation, if desired.

Using the points 114 and 118, a slope is determined and a linear function model 126 is calculated. Using the linear model 126, the processing system can calculate the estimated threshold stimulus 124 at which the model 126 crosses the threshold 104, or can calculate the point 123 at which model 126 crosses the EMG zero level. Because the EMG trend increases in a nearly linear manner in portion 130 of the trend, the model 126 provides an adequate estimator of the threshold stimulus 112 whether point 122 or 123 is calculated.

In addition to points 114 and 118 used to create the linear model 126, a third stimulus point, for example point 108, can be factored in to improve or verify the accuracy of the estimated threshold stimulus. In certain embodiments, three points may be used to perform a linear regression, and can include calculating and reporting a reliability factor that indicates the expected accuracy of the model. The linear regression may make use of two above-threshold points, such as points 114 and 118, and one below-threshold point, such as 108, to include the desired threshold within the range of detected EMG response points. A third point may also be used to create additional linear models, for example a linear model between point 108 and 114 or between point 108 and 118, to calculate additional threshold estimations. The additional estimations can be used to verify the precision of the linear models by detecting whether the multiple estimations are clustered or spread over a wide range of stimulus levels.

In order to obtain the two EMG responses at points 114 and 118 after delivering respective stimulus signals at levels 116 and 120, multiple approaches may be employed. For example, the delivered stimulus pulses at levels 116 and 120 may be part of a sequence of stimulus pulses that are delivered until two EMG responses are detected above the threshold 104. A first stimulus may be delivered at stimulus level 110, and the EMG response may be detected at point 108 in trend 102. The neuromonitoring system determines that the point 108 lies below the threshold 104 and increases the level of the delivered stimulus to level 116. When the EMG response to level 116 is detected at point 114, the stimulating and monitoring system can determine that the point 114 lies above the threshold 104 and deliver a final stimulus at level 120 to obtain a second EMG response, at point 118, that is above the threshold 104. Additional points may also be obtained along the curve by stimulating and monitoring the EMG response. The system then ends stimulus delivery and creates the model 126 using the two points 114 and 118, which are above the threshold 104.

In other implementations, the first stimulus, for example at level 116, may be a set initial stimulus level that is delivered to the patient. When the stimulus 116 is delivered and the EMG response is measured at the first stimulus point 114, the second stimulus level 120 may be set based on the magnitude of the EMG response at the first stimulus point 114. For example, when the point 114 lies within the second portion 130, the stimulating and monitoring system may slightly increase the stimulus to level 120 in order to obtain the second point 118. However, if the first stimulation fell below the threshold 104, for example at stimulation level 108, the neuromonitoring system may use a greater increase in stimulus in order to obtain a second point that would fall within the second portion 130 or the third portion 132. By contrast, if the first stimulation fell within the third portion 132 or towards the upper end of portion 130, the neuromonitoring system may decrease the stimulus level to obtain a second stimulation and response point falling within either the first portion 128 or the second portion 130.

Once an initial determination of the stimulation threshold is made, subsequent determinations may start with stimulation levels that are selected in situ based on the prior value of the stimulation threshold. Stimulus levels may also be selected from a model of stimulus signals and EMG responses for a particular nerve, or a general nerve stimulation model. In some implementations, the model used to select the stimulus signals may be specific to the nerve being monitored and may be created from a series of test stimulus signals and detected test neuromuscular responses. A series of stimulus signals having increasing levels, for example increasing current, voltage, pulse width, charge, or a combination thereof, can be delivered at or near the modeled nerve, and EMG responses for each delivered stimulus can be recorded and plotted. A curve or other model is then fit to the data, and the curve is used in further modeling of the nerve to select the stimulus level or levels from desired sections of the model, for example at or before the nearly linearly increasing portion of the trend shown in FIG. 1 and discussed above.

The model 126 uses two points, 114 and 118, that fall on the trend 102 above the threshold 104 and within the second portion 130. Other stimulation levels may be used that fall either outside of the second portion 130 or that fall below the threshold 104 while still maintaining an adequate estimation of the stimulus 112 that produces the threshold response at point 106 or stimulus 110 at transition point 108. Locating the stimulus 112 to a very precise degree often requires the delivery of a large number of stimulations in order to narrow to a small range of stimuli, from one stimulus that does not evoke an EMG response to a second stimulus that does evoke the response. In the interest of providing a surgeon with a quick indication of nerve proximity or bone integrity, the estimation approach may allow for a wider resolution in order to reduce stimulations and increase speed. Thus, the small distance between the estimated stimuli 124 or 125 and the actual thresholds 112 or 110 may be an acceptable range, and the stimuli 124 or 125 an adequate estimation for the purposes of neuromonitoring during surgery.

Figure 7:
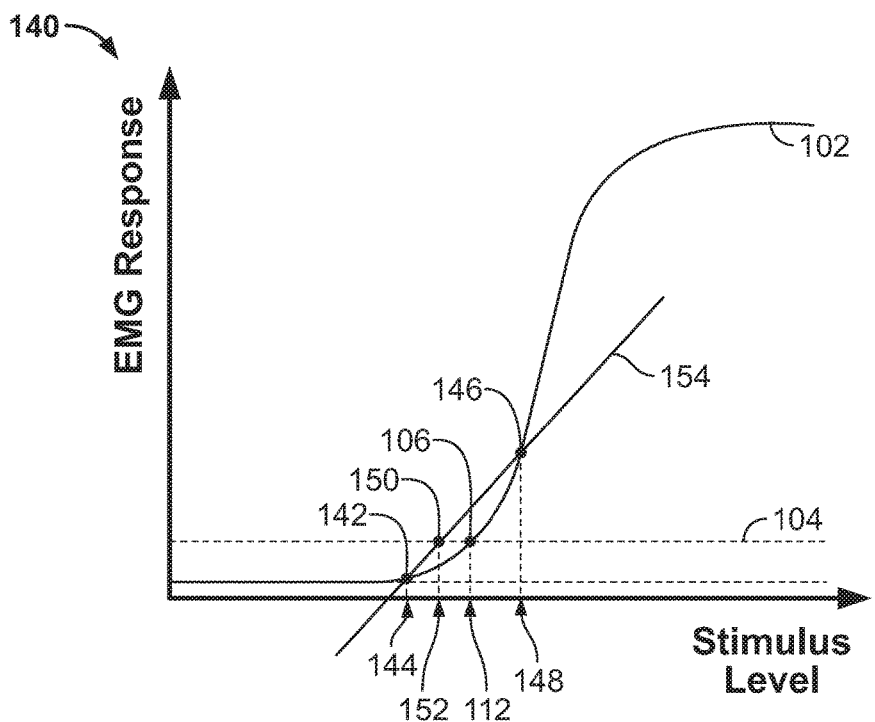

FIG. 7 shows a graph 140 that illustrates an estimation approach that utilizes a first EMG response at point 142, below the threshold 104, and a second EMG response at point 146 that lies above the threshold 104 to obtain an estimate of the threshold stimulus 112 or 110 that produces the threshold response at point 106 or 108 along the trend 102. As shown in the graph 140, the linear function model 154 is created by calculating a slope between the point 146 and the point 142. The model 154 can be used to provide an adequate estimated stimulation threshold 152 that would produce a threshold response at point 150 along the model 154 or can be used to estimate a threshold stimulus 144 where model 154 crosses the EMG zero, at/or near point 142. Although the point 142, corresponding to the first delivered stimulus level 144, falls below the threshold 104, an acceptable estimated threshold stimulus level 152 or 144 can still be calculated. Thus, when stimulation is delivered at two levels 144 and 148 that do not both produce EMG responses that lie on the nearly linear portion of the trend 102, the linear estimating model 154 can still be sufficient to provide an estimated stimulation threshold while requiring only two stimulation signals to be delivered to a patient. In some implementations, the calculation may use three stimulation signals and three neuromuscular responses—one stimulation signal that does not produce an above-threshold response and two stimulation signals that produce above-threshold responses in the nearly linear portion of the trend curve.

Figure 8:
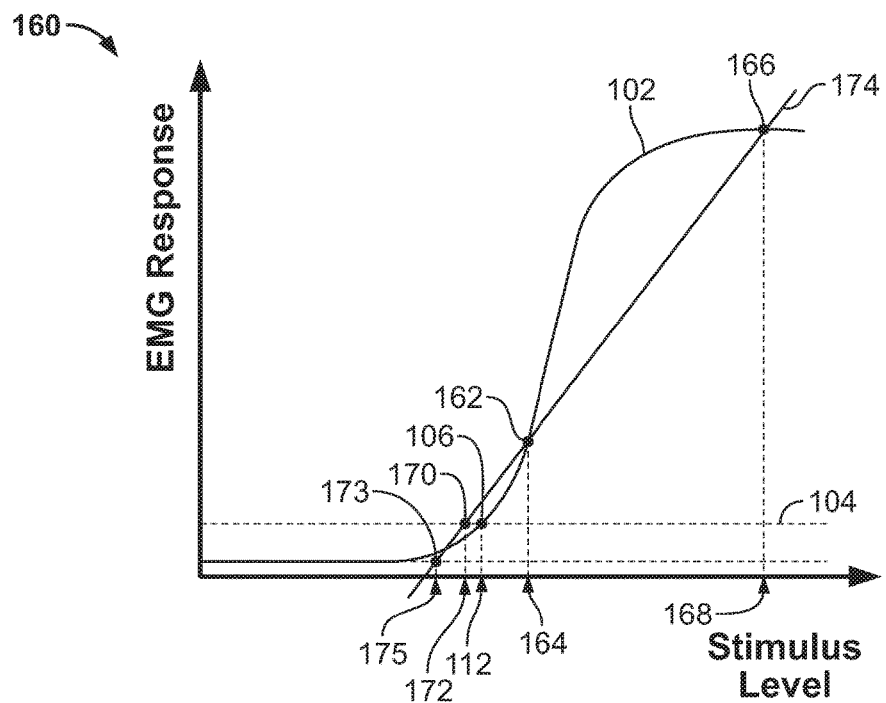

FIG. 8 shows a graph 160 illustrating an estimation approach that uses a first EMG response at point 162 in the nearly linear portion of the trend 102 and a second EMG response at point 166 in the plateau region of the trend 102. The point 162 corresponds to a delivered stimulus level 164, while the point 166 corresponds to a delivered stimulus level 168. From the two EMG responses at points 162 and 166, a slope is calculated, similar to the approaches in FIGS. 6 and 7, and a linear function model 174 is used to approximate the trend 102. From the model 174, the threshold stimulus level 112 can be estimated as level 172 producing the EMG response at point 170 on the model 174 or can be estimated as level 175 producing an EMG response at point 173 at the zero EMG level of model 174.

Figure 9:
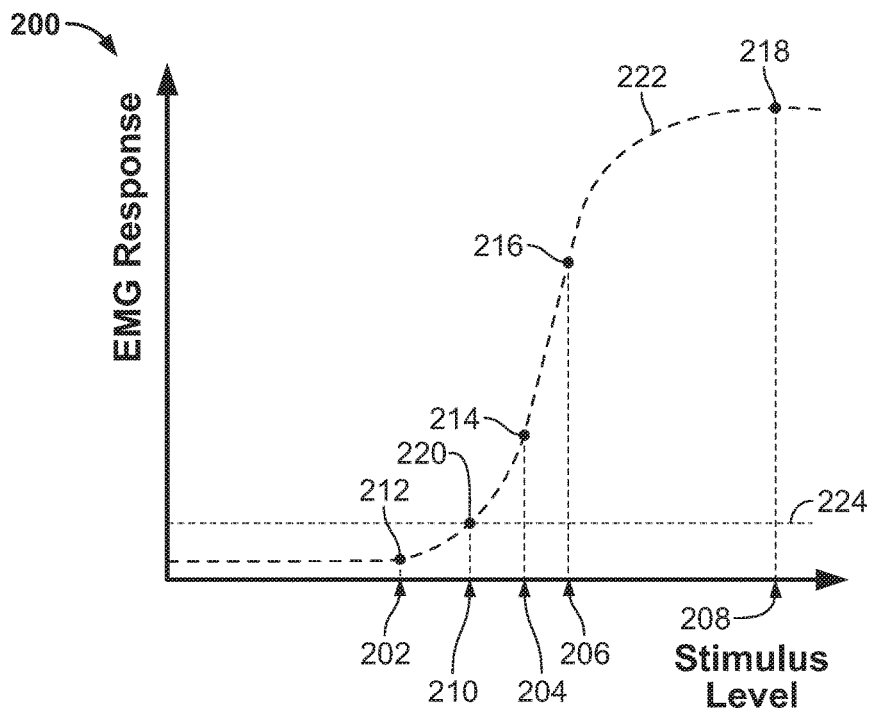
FIG. 9 depicts an illustrative estimation of a threshold stimulation using curve-fitting modeling.

While linear estimation approaches such as those shown in the FIG. 6-8 may provide accurate estimations of threshold stimulus levels, other approaches may use the generally known sigmoidal shape of the typical trend 102 to apply a curve-fitting approach that may produce more accurate estimations, particularly more accurate estimations over a wider range of delivered stimulus levels. Graph 200 in FIG. 9 shows an example of a curve-fitting estimation approach using more than two stimulations. In this approach, four stimulation signals are delivered at levels 202, 204, 206 and 208. The delivered stimuli elicit four EMG responses detected at points 212, 214, 216 and 218. As shown in the graph 200, the first point 212 falls below the threshold 224 while the other three points 214, 216 and 218 fall above the threshold 224. This indicates that the desired threshold stimulus level falls somewhere between the delivered stimuli at 202 and 204.

In order to estimate the minimum threshold stimulus, the four detected EMG responses 212, 214, 216 and 218 are input into a sigmoid function modeling process that uses the four detected responses to estimate a model 222 that mimics the known typical EMG response pattern. From the model 222, an estimated minimum threshold stimulus level 210 can be calculated from the point 220 that falls on the threshold 224 in the model 222. The curve-fitting approach may thus provide estimations of the minimum threshold while still limiting the number of delivered stimulations that measure EMG responses to as few as three or four stimulations.

Figure 10:
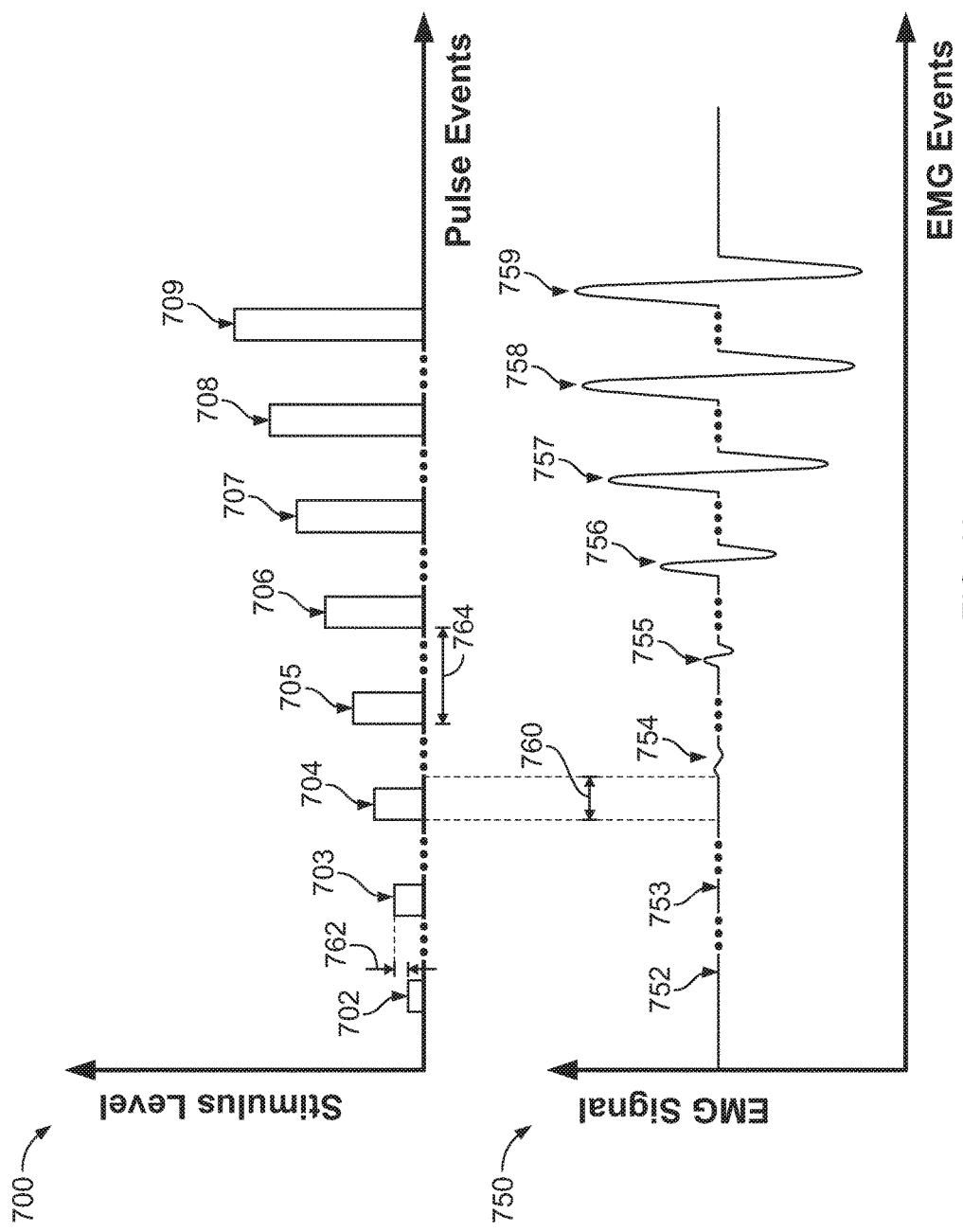
FIG. 10 depicts an illustrative sequence of test stimulus signals and a corresponding illustrative sequence of detected EMG responses.

In order to create the curve fit model 222 shown in FIG. 9 to assess baseline excitability for a particular nerve or to select future testing stimulus levels, data for a series of pulses and corresponding EMG responses is obtained for the nerve. FIG. 10 shows a sequence of stimulus signals in graph 700 and corresponding EMG responses in graph 750. In particular, FIG. 10 shows eight pulses 702-709 and their respective EMG responses 752-759. The stimulus level of each of the pulses 702-709 is increased relative to the previous pulse. In particular, the level of each subsequent pulse is increased by a constant increment 762, shown between pulses 702 and 703. The increase may be the result of adjusting current, voltage, pulse width. charge, pulse shape, any other suitable characteristic, or a combination thereof. As a result of the increased level of each successive stimulus pulse, the magnitude of the sensed EMG responses in graph 750 increases with each subsequent pulse. For example, responses 752 and 753 show little, if any, deviation from the EMG base line in response to pulses 702 to 703, while pulses 758 and 759 show large deviations from the EMG baseline in response to the larger pulses 708 and 709.

The pulses and responses shown in graphs 700 and 750 depict a stimulation and monitoring approach useful for measuring one or more responses that may be plugged into the extrapolation or estimation technique discussed above with respect to FIGS. 6-9. For example, the train of pulses shown in graph 700 may continue with constant increment 762 between each pulse until two EMG thresholds are detected in graph 750. Once the two pulses above the threshold are detected, the system can stop delivering the stimulation pulses and use the last two above-threshold EMG responses and the corresponding stimulus levels to use as input to the estimation or curve-fitting calculations used to estimate the threshold stimulus. The stimulus train shown in graph 700 may start at a low level, as shown for pulse 702, and increase until the two above-threshold responses are detected, or may start at a higher level that is known to be at or near the threshold level.

The pulses delivered in graph 700 not only increase in level by the increment 762, but are temporally spaced apart by a constant time period 764. The period 764 between each pulse is set such that the muscle innervated by the monitored nerve may recover after a contraction or EMG response. The time period 764 can be set such that it is greater than or equal to the known refractory period of the monitored nerve and the innervated muscle. For example, the time period 764 is set to be greater than the amount of time that a muscle is known to have a refractory period during which it recovers before another full stimulation and response is possible. In addition, the time period 764 can take into account the signal transit time that is required for a nerve signal to travel from the point of stimulation to the innervated muscle before contraction begins. This signal transit time is shown by time period 760 between the beginning of the pulse 704 and the beginning of the sensed EMG response 754 corresponding to that pulse. In addition to taking into account the time that the neuron stimulated by pulse 704 and the muscle responding at peak 754 need in order to recover from the stimulus, the time period 764 can also take into account the time period 760 required for the transit of the stimulation signal from nerve to muscle.

The transit period 760 may also be used to time EMG monitoring and eliminate noise from the sensed EMG signal shown in graph 750. For example, the known signal transit delay between stimulus pulse and EMG response can be used to create predetermined monitoring windows during which the system monitors for EMG responses, as shown in graphs 770 and 780 in FIG. 11. Graph 770 shows a series of three stimulus pulses 772, 774 and 776, while graph 780 shows a series of corresponding EMG responses 782, 784 and 786. Each of the EMG responses is offset from its corresponding stimulus pulse by a time period. For example, the EMG response 782 trails its corresponding stimulus signal 772 by a time period 790. As discussed above, this time period 790 arises due to the transit time required for the stimulus signal to travel from the point of stimulation to the innervated muscle and for the innervated muscle to begin the contraction that produces the EMG response 782.

The transit time period 790 is generally known for a given pair of nerve and innervated muscle. This known time value can improve the EMG monitoring used to produce the graph 780 by only detecting or analyzing responses in a time window during which EMG responses are expected. For example, a sensing module is configured to apply a sensing window 794 to an EMG response curve indicative of the time window in which an EMG response is expected. After a stimulus pulse 774, the neuromonitoring system ignores EMG signals outside of the sensing window 794. The sensing window 794 is a period of time that is predetermined and is offset from its corresponding stimulation pulse 774 by a time period 791 that is shorter than period 790, the known transit time between the nerve and the muscle. The window 794 is created by starting the window 794 at the time period 791, at the left boundary 793 of the window. The window 794 then continues for the set time width of the window, ending at right boundary 795. By detecting and analyzing only EMG signals received within the sensing window 794, the system may cut out any noise detected before the left boundary 793 of the sensing window 794 or after the right boundary 795 of the sensing window 794. This eliminates the possibility of detecting any false positives caused by noise outside of the sensing window 794 during which the true EMG response occurs. Likewise, a predetermined sensing window 796 may be set in response to the stimulation signal 776. Like the sensing window 794, the sensing window 796 is offset from the stimulation pulse 776 by the time period 791 and has a width that is equal to the sensing window 794. Programming the system to use this window can eliminate false positives from noise detected outside of the sensing window 796 and help identify the true EMG response 786 in response to the stimulation 776.

Figure 11:
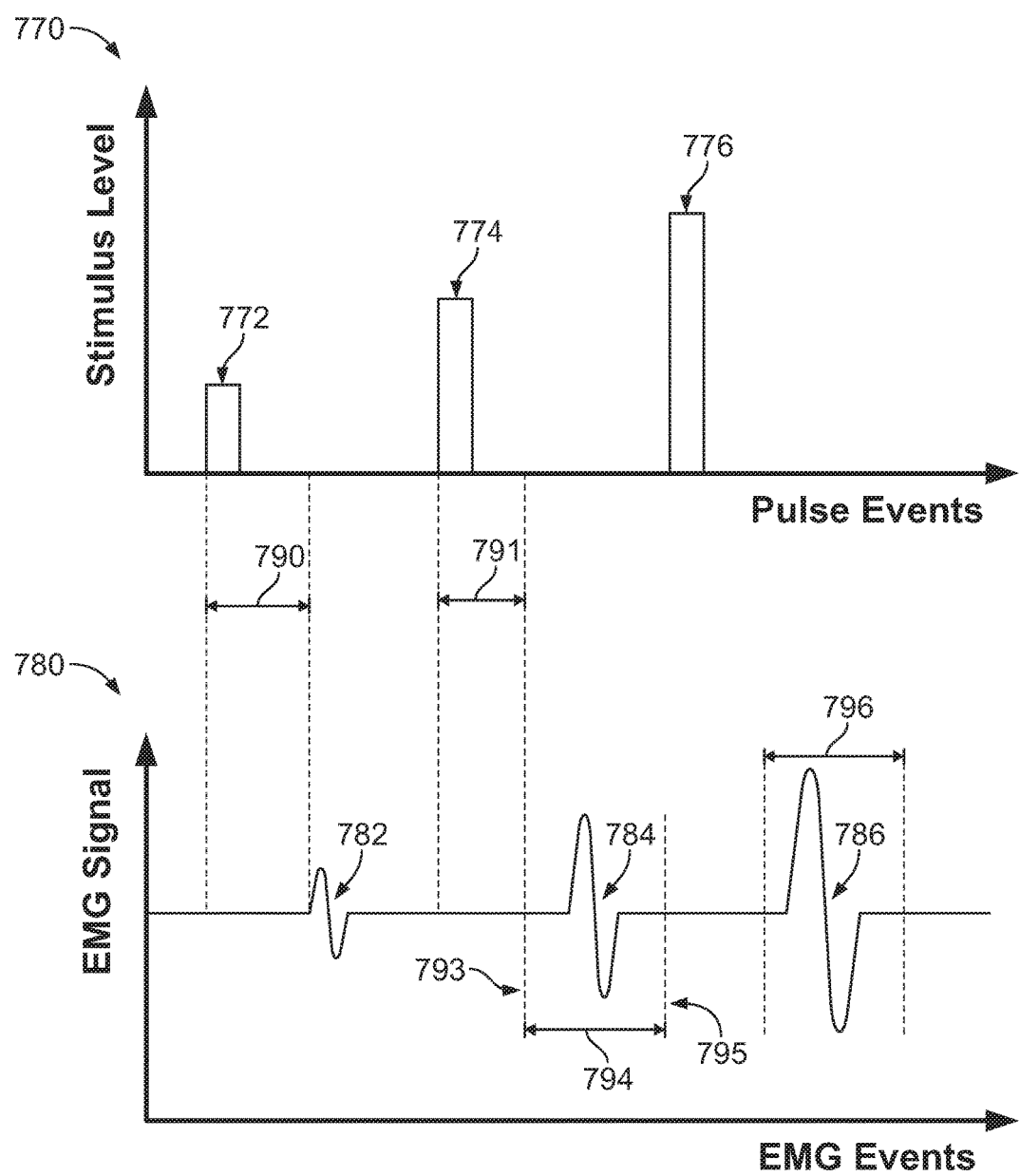
FIGS. 11 and 12 depict illustrative sequences of stimulus signals and corresponding detected EMG responses.
Figure 12:
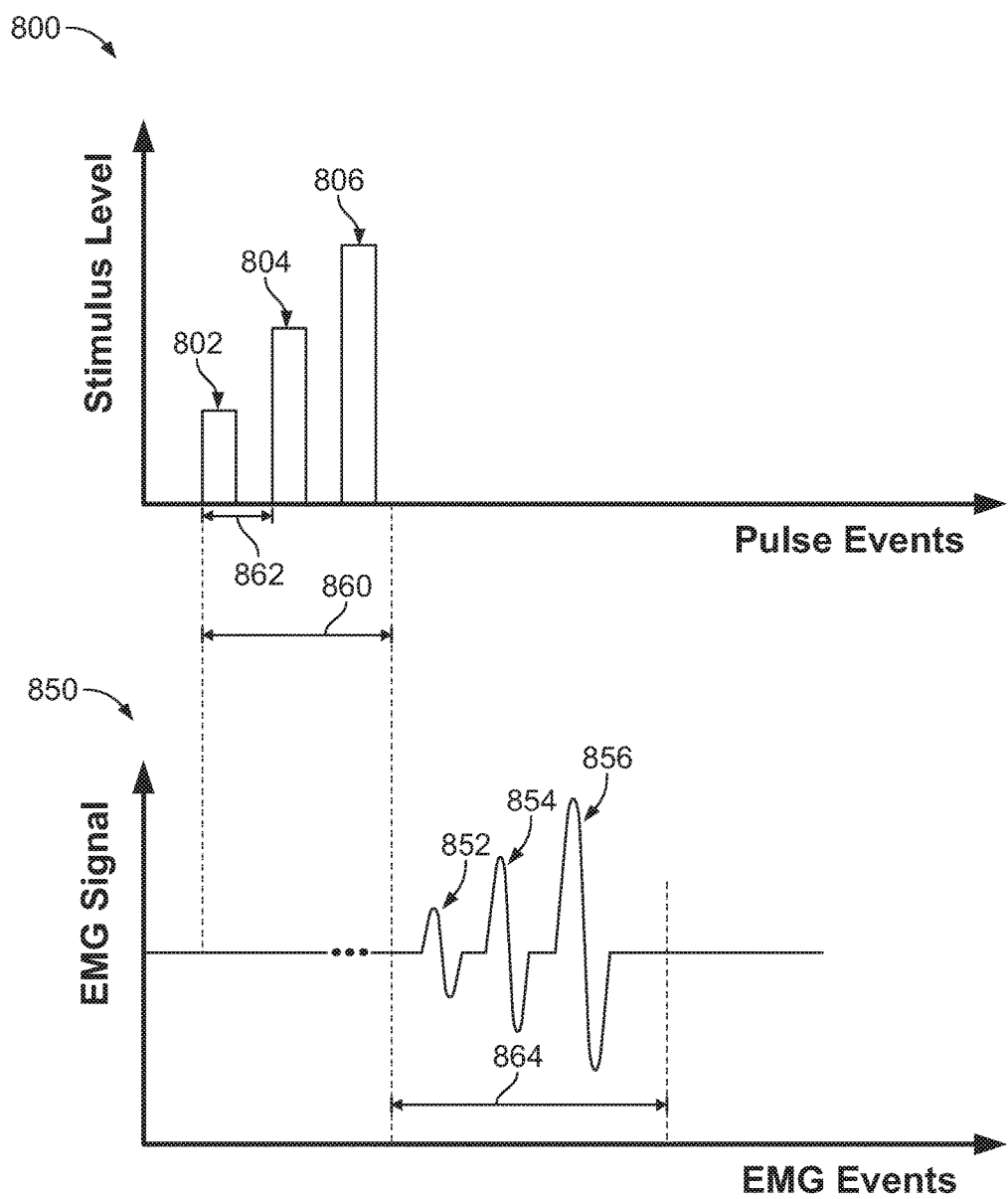

In addition to using the known transit time between nerve and muscle to cut out noise outside of sensed EMG windows, the transit time may also be used to decrease the amount of time required for the delivery of sequential stimulation pulses and the detection of subsequent EMG responses. While FIG. 11 shows a sequence in which a single pulse 772 is delivered followed by detection of an EMG response 782 before the next stimulation pulse 774 is delivered, the use of time windows may compress the stimulation signals shown in graph 770 such that two or more stimulation signals may be delivered before any EMG response is detected in response to the first stimulation. The known transit time between each stimulation and EMG response is then used to relate each sensed EMG response to its corresponding stimulation pulse, as shown in FIG. 12.

Graph 800 shows three stimulation pulses 802, 804 and 806, each of which is delivered before any EMG response is detected in the corresponding EMG response graph 850. As shown, each of the three stimulus signals 802, 804 and 806 is delivered before the first EMG response 852 is detected in response to the stimulus signal 802. The time period 860 shown in FIG. 12 between the beginning of the stimulus pulse 802 and the corresponding EMG response 852 is long enough that the three stimulation pulses can be delivered within the time 860 while still allowing both the nerve and innervated muscle to recover from each subsequent pulse. The time period 862 between each stimulus pulse, for example between pulse 802 and 804, is set so that the time between the pulses is at least as long as the refractory period of the nerve and muscle. After the three pulses 802, 804 and 806 are delivered, a sensing module may detect EMG responses during a sensing window 864 that starts at time period 860, before the time of the expected EMG response for the pulse 802 and ends after the expected time of the corresponding EMG response for pulse 806. Within the sensing window 864 in which the three responses 852, 854 and 856 are detected, each individual response is related to its corresponding stimulus pulse by using the known transit time between the monitored nerve and muscle. The delivery of pulses and sensed EMG responses shown in graphs 800 and 850 can be compressed in time relative to the stimulus pulses and EMG responses shown in graphs 770 and 780 of FIG. 11. This approach eliminates the need to wait the full signal transit time after each pulse before delivering a next pulse, and thus may allow for quicker and more efficient localization and distance calculations in neural monitoring.

Figure 13:
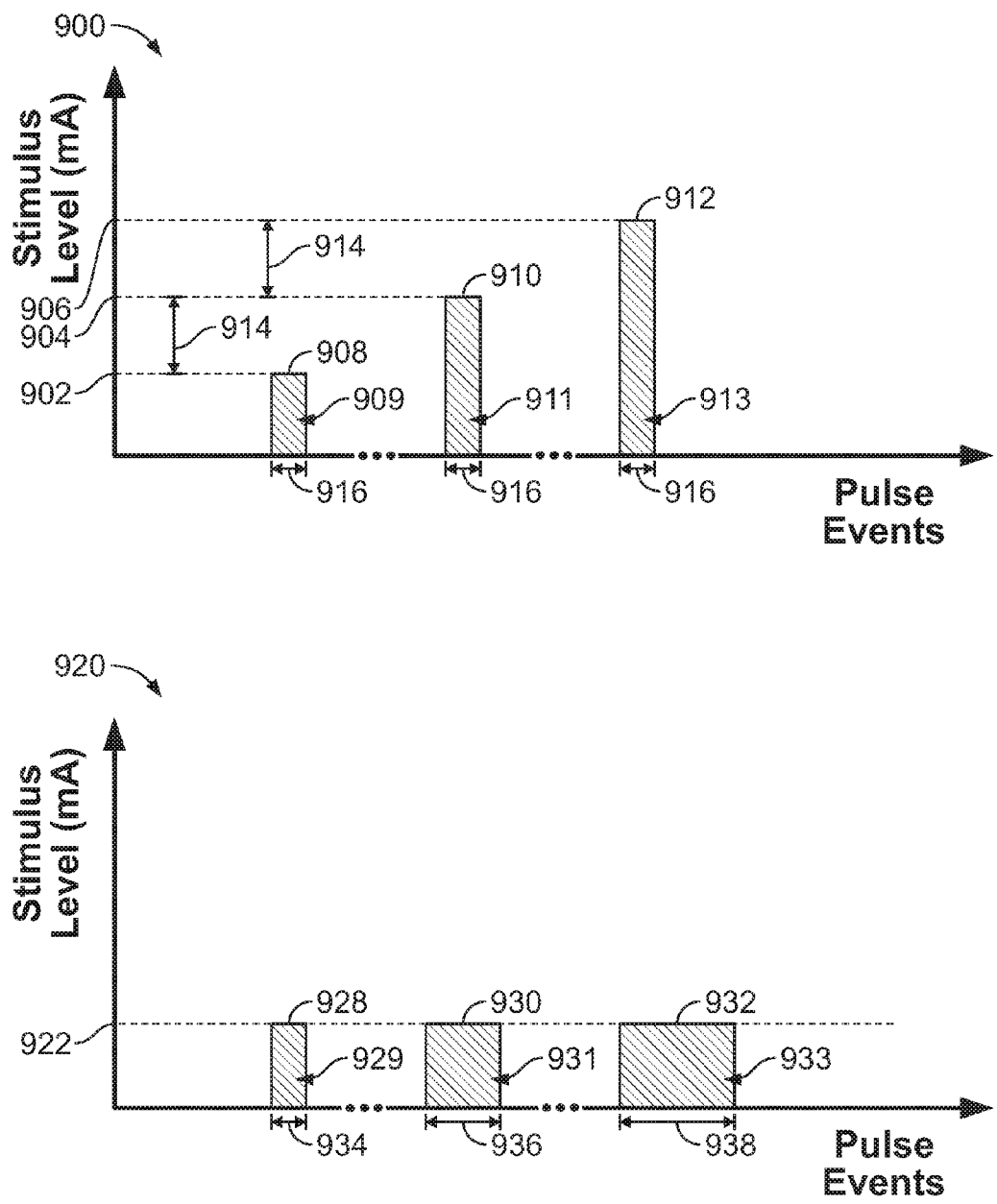
FIG. 13 shows an illustrative comparison of stimulus signals having increasing currents and stimulus signals having increasing pulse widths.

The approaches discussed above utilize increasing levels of stimulus signals in order to detect and locate multiple points along an EMG response curve, for example the typical response curve shown in FIG. 1. In addition to (or in lieu of) the current of a stimulus signal, other stimulus characteristics, for example voltage or pulse width, may be used to produce the different stimulus levels and locate various points along the EMG response trend and determine stimulation characteristics that may be used to guide a surgical tool. FIG. 13 shows examples of using varying current and varying pulse width to produce a neuromonitoring approach similar to the monitoring and detection approaches discussed above. In a first graph 900, three stimulus pulses 908, 910 and 912 are shown with a constant pulse width but varying current, while graph 920 shows three stimulus pulses 928, 930 and 932 that are delivered at constant current but varying pulse width. In graph 900, the level of each successive stimulus signal increases as the current is increased by a constant increment 914 between each pulse. For example, stimulus 908 is delivered at a current 902 while the next stimulus 910 is delivered at a higher current 904, and finally stimulus 912 is delivered at the higher current 906. Each of the stimulus pulses 908, 910 and 912 has the same pulse width 916, and thus the increasing current from 908 to pulse 912 increases the amount of charge delivered for each subsequent stimulus pulse. Graph 920, on the other hand, depicts the three stimulus pulses 912, 930 and 932 delivered at a single constant current 922 that does not increase from pulse to pulse. The pulse widths of the pulses 928, 930 and 932, however, do increase for each subsequent pulse, from the pulse width 934 for stimulus 928 to the pulse width 936 for pulse 930 and finally the pulse width 938 for stimulus 932.

Both the increasing current in the pulses of graph 900 and the increasing pulse width of the pulses in graph 920 provide a larger stimulus (or higher total coulombs) to the nerve for each subsequent delivered pulse. Though the pulse width does not change in graph 900 and the current does not change in graph 920, each of the three pulses shown in each graph may elicit increasing responses in an innervated muscle as a result of the charge delivered to the tissue. For example, stimulus 908 has a total charge that is depicted by the area 909 of the pulse, while the stimulus 928 has a corresponding area 929 that depicts the quantitative amount of charge delivered during that pulse. Because the pulses 908 and 928 are delivered at substantially the same currents 902 and 922 and have substantially the same pulse width 916 and 934, these pulses are essentially equivalent and would elicit the same response in an innervated muscle. The second pulses 910 and 930 have differing shapes, however, they deliver a similar cumulative amount of charge to the nerve during the pulses, as the area 911 of pulse 910 is and the area 931 of the pulse 930 are similar. In pulse 910, the current of the pulse is approximately doubled relative to the pulse 908, and thus the area 911 is double the area of 909 of stimulus 908 and the amount of charge delivered by stimulus 910 is doubled. For stimulus 930, the current 922 is the same as the pulse 928, but the pulse width 936 is double the pulse width 934 of the stimulus 928. Thus, the charge, or area 931 of the stimulus 930, is approximately doubled relative to the stimulus 928. As a result, the pulses 910 and 930 deliver charges to a nerve and that would both elicit a response from the innervated muscle. Finally, the pulse 912 is increased again by the current increment 914 relative to stimulus 910 and has a level that is three times the level of the first pulse 908, an increase by 50% over the stimulus 910. This results in an area 913 of the pulse 912 that is approximately three times the area of the original pulse 908. Likewise, in graph 920, the pulse 932 has a pulse width 938 that is three times the original pulse width 934 and 50% larger than the pulse width 936. The resulting area 933, or the quantitative charge delivered by the pulse 932, is approximately three times that of the original pulse 928. Thus, the pulses 932 and 912 would also be expected to elicit EMG responses from the innervated muscle.

The varying pulse width approach shown in FIG. 13 may be used to navigate the typical EMG response curve shown in FIG. 1 and locate multiple points along the curve that can be used to determine or estimate a threshold stimulation. The varying pulse width approach can be used if a constant current, for example current 922 shown in FIG. 13, is desired for stimulus pulses rather than an increasing current that may reach levels that can cause discomfort for a patient. Constant current is not required, and pulse width may be varied along with current, but may be preferred to keep current at a known constant for delivered stimulations. In addition, lower current can be used in a varying pulse width approach to reduce a power demand on a system, which may be useful in decreasing energy demands of a neuromonitoring device, particularly in the case of battery-powered devices. For battery powered or wireless stimulus devices, the reduction in power consumption provided by the varying pulse width can provide for a longer device life or longer battery life between charges.

Stimulation signals allow an operator to control multiple characteristics of stimulus pulses to control the level of stimulus delivered to a patient. For example, the voltage, current, pulse width, charge, shape, or other characteristic of a pulse can be programmed for a particular application in order to achieve the desired stimulus level. Changes in one or more of these characteristics can increase the stimulus level and adjust stimulus signals to identify a combination of the stimulus characteristics that stimulates a nerve. An example showing the effect of changing one of multiple characteristics can be shown by the relationship between a signal strength, for example current amplitude or voltage, and signal duration, for example pulse width.

Figure 14:
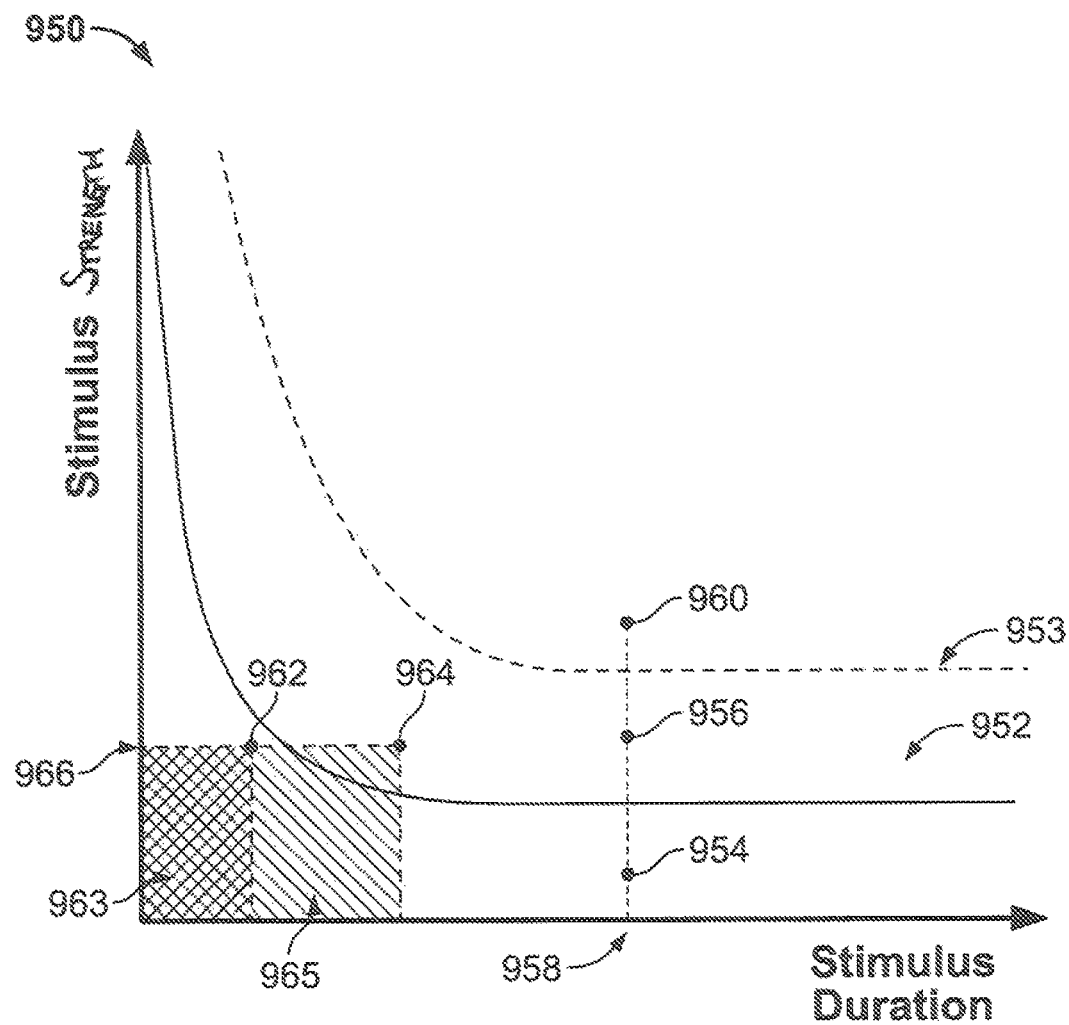
FIG. 14 shows an illustrative strength-duration curve.

The relationship between stimulus strength, for example current amplitude or voltage, and stimulus duration, for example pulse width, is shown as one example of adjusting multiple stimulus characteristics in a threshold curve for a given nerve, for example the curve 952 shown in the graph 950 of FIG. 14. Curve 952 depicts the relation between stimulus strength and duration required for stimulation of a particular nerve. The curve for a particular nerve varies from nerve to nerve based on the excitability of the nerve. The curve 952 depicts the minimum proportion between stimulus level and duration of stimulus pulse that will cause stimulation of a nerve and contraction of a muscle innervated by the nerve. For example, a stimulus pulse delivered with a pulse width 958 and a level at point 954 lies below the curve 952 and thus would not cause stimulation of the nerve depicted by the curve. If the stimulus pulse was increased up to point 956 but remained at pulse width 958, the resulting stimulus would cause stimulation of the nerve and corresponding muscle, as point 956 lies above the curve 952. The second curve 953 in graph 950 depicts a second nerve that is less excitable than the nerve depicted by curve 952, and the second nerve 953 still would not be stimulated by the pulse delivered at point 956, as that point lies below the curve 953. If, however, the stimulus level was again increased to point 960, that point lies above both curves 952 and 953, and thus a pulse delivered at point 960 having the pulse width 958 would stimulate either of the nerves shown by the two curves.

With respect to pulse width variation, the stimulus delivered at point 962 in the graph 950 at level 966 would not stimulate the nerve because that point lies below the curve 952. If, however, the pulse width was increased to point 964, the stimulus delivered at 964 would stimulate the nerve and muscle, as that point now lies above the curve 952. The charge delivered at each of points 962 and 964 is depicted by areas 963 and 965, respectively. This area under the curve shows a quantitative amount of charge at point 964 that is larger than the charge at point 962. The charge shown by area 963 is not sufficient to stimulate the nerve, while the larger charge at point 964 is sufficient and triggers the nerve. Thus, by varying at least one of stimulus level and duration, a neuromonitoring system can be employed to find at least one point that lies below the curve and one point that lies above the curve either at constant voltage, constant current or constant pulse width.

The EMG responses detected by varying pulse widths of stimuli held at a constant current is shown in the graphs 1000 and 1050 in FIG. 15. Three stimulus pulses 1002, 1004 and 1006 are delivered to a nerve at a constant level 1008. In response to the stimulus pulses, three EMG responses 1052, 1054 and 1056 are detected in a muscle innervated by the stimulated nerve. As shown, the magnitude of each successive EMG response increases as the pulse width of each stimulus pulse increases, from a width 1001 for pulse 1002 to a width 1003 for pulse 1004 and a width 1005 for pulse 1006. The increase in pulse width at constant level creates a larger charge delivered to the nerve for each successive pulse, and thus the magnitude of EMG responses increases from response 1052 to responses 1054 and 1056. The pulse width of successive stimuli may be increased until a EMG response greater than or equal to an EMG threshold is detected. The threshold, for example threshold 1058, may be applied to the EMG detected signal to determine whether a threshold response is present, as discussed above. As shown in graph 1050, pulses 1002 and 1004 elicit below-threshold responses 1052 and 1054 while a third pulse 1006 elicits an above-threshold response 1056 from the muscle. Using this increasing pulse width approach, a neuromonitoring system is able to determine pulse widths both below and above the desired EMG threshold, for example pulse widths 1001 and 1003 below the threshold and pulse width 1005 above the threshold for the constant level 1008.

The above-threshold pulse width 1006 determined in FIG. 15 may be reported, or may be used to calculate the total charge in coulombs required to elicit the above-threshold response. As an alternative, the pulse width may also be plugged into an estimation calculator, such as the extrapolation and estimation or curve-fitting approaches discussed above, in order to estimate the minimum pulse width required to elicit a threshold response without actually delivering any stimuli at the calculated pulse width. While the stimuli and corresponding responses shown in FIG. 15 alternate between stimulus and EMG detection, multiple pulses may be delivered before any EMG response is detected, as discussed above with respect to increasing current pulses in FIG. 12. For example, depending on the width of each pulse and the delay between a pulse and the corresponding muscle reaction, the three stimulus pulses 1002, 1004, and 1006 may be delivered before the first EMG response 1052 is detected.

EMG responses and corresponding stimulus pulse widths can be used to determine an estimate of the minimum stimulus level. For example in terms of pulse width for a given constant current, required to elicit a threshold neuromuscular response from the monitored nerve and muscle pair. The increasing pulse width stimuli and corresponding EMG responses can be located along the EMG response curve shown in FIG. 1 and used to create linear or curve fit models to calculate an estimated minimum pulse stimulus strength, in terms of pulse width, as discussed above with respect to FIGS. 6-9. In other implementations, rather than modeling and estimating the threshold, a neuromonitoring system may apply additional stimuli at additional pulse widths to narrow a range within which the minimum threshold may lie until a range having a width less than or equal to a desired resolution is determined. This approach is illustrated in FIGS. 16-19.

In FIG. 16, a sequence of stimulus signals having increasing pulse widths is shown in graph 1100, and corresponding detected EMG responses to the delivered stimuli are shown in graph 1120. The first stimulus 1102, having a pulse width X, delivered in the vicinity of a nerve results in a detected EMG response 1122 trailing the stimulus. A neuromonitoring system applies an upper EMG threshold 1130 and a lower EMG threshold 1132 defining deviations from the EMG baseline 1134 that are great enough for EMG signals to be considered true EMG responses, and the system determines whether the response 1122 is greater than or equal to either of the thresholds. Certain neuromonitoring systems and methods may use correlation, for example the correlation approach discussed above with respect to FIG. 5, rather than EMG signal voltage to differentiate above-threshold and below-threshold EMG responses. When the system determines that response 1122 is does not meet either of the thresholds 1130 and 1132, a second stimulus 1104 is applied having a pulse larger than the pulse width of stimulus 1102.

The pulse width of the second stimulus 1104 is increased by an increment X, resulting in a pulse width of 2× for the stimulus. The larger pulse width delivers more charge in the vicinity of the monitored nerve, and thus is expected to elicit a greater EMG response from the monitored muscle. This is shown in graph 1120 by the response 1124, which trails the stimulus 1104 and deviates from the EMG baseline 1134 to a larger degree than the previous response 1122. The response 1124, however, does not meet either of the threshold 1130 or 1132, so a third stimulus 1106 is scheduled. The stimulus 1106 has a pulse width that is increased by X relative to the pulse width of stimulus 1104, making the pulse width of stimulus 1106 3×. A response 1126, which is larger than the responses 1122 and 1124, is then detected, but does not meet either of the thresholds 1130 or 1132. A fourth stimulus 1108 having a pulse width increased by X relative to stimulus 1106 to 4× is then delivered, and a fourth response 1128 is detected in response to the stimulus. Following the fourth response 1128, the neuromonitoring system is able to determine that the pulse width of stimulus 1108 has elicited a threshold EMG response 1128 from the monitored muscle, and thus the pulse width of stimulus 1108 is either greater than or equal to the pulse width required to elicit a response that equals the threshold.

Figure 17:
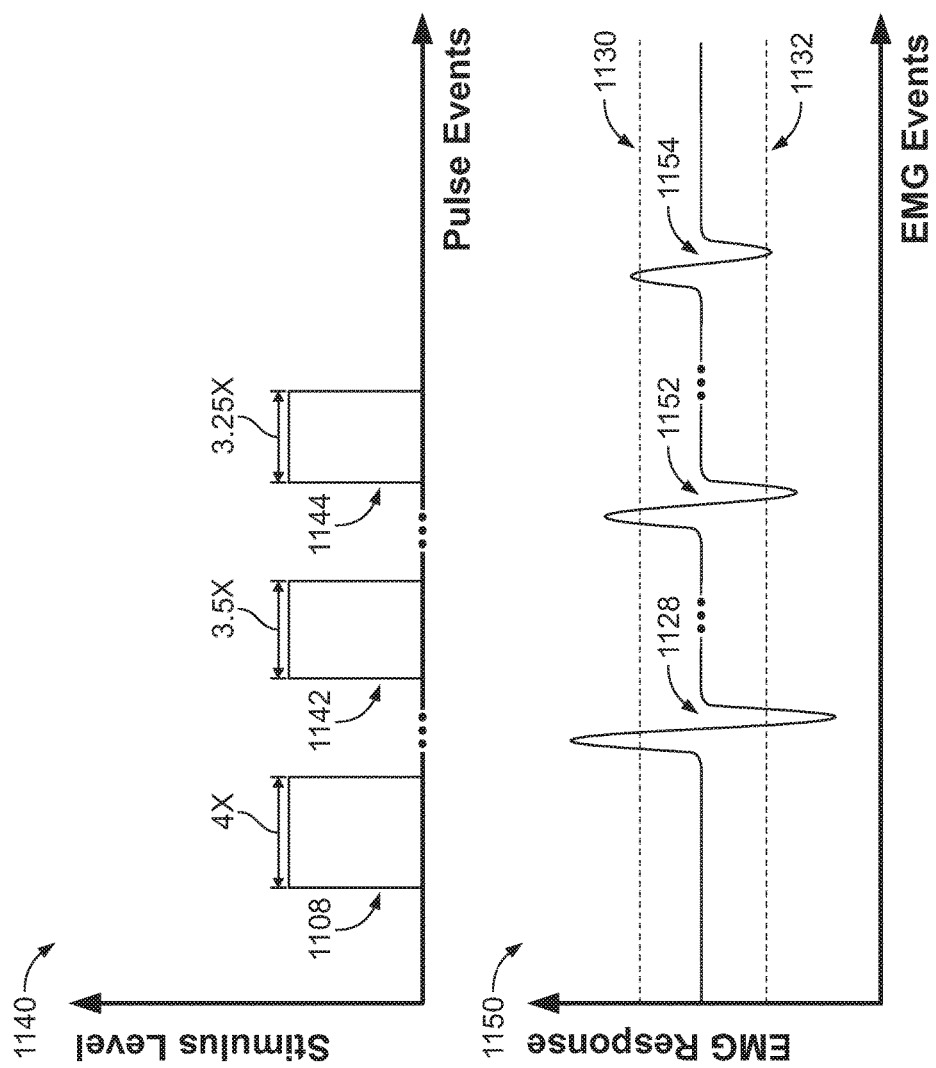
Figure 18:
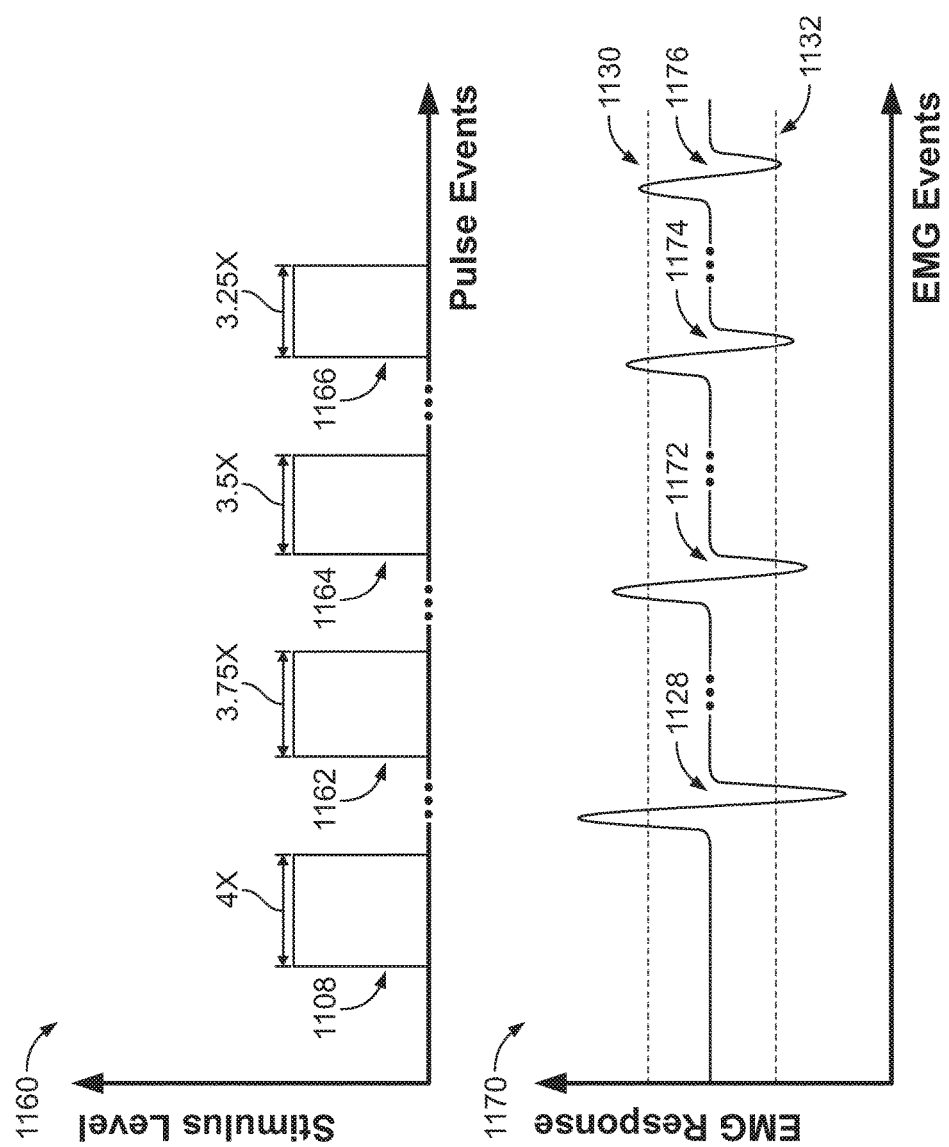
Figure 19:
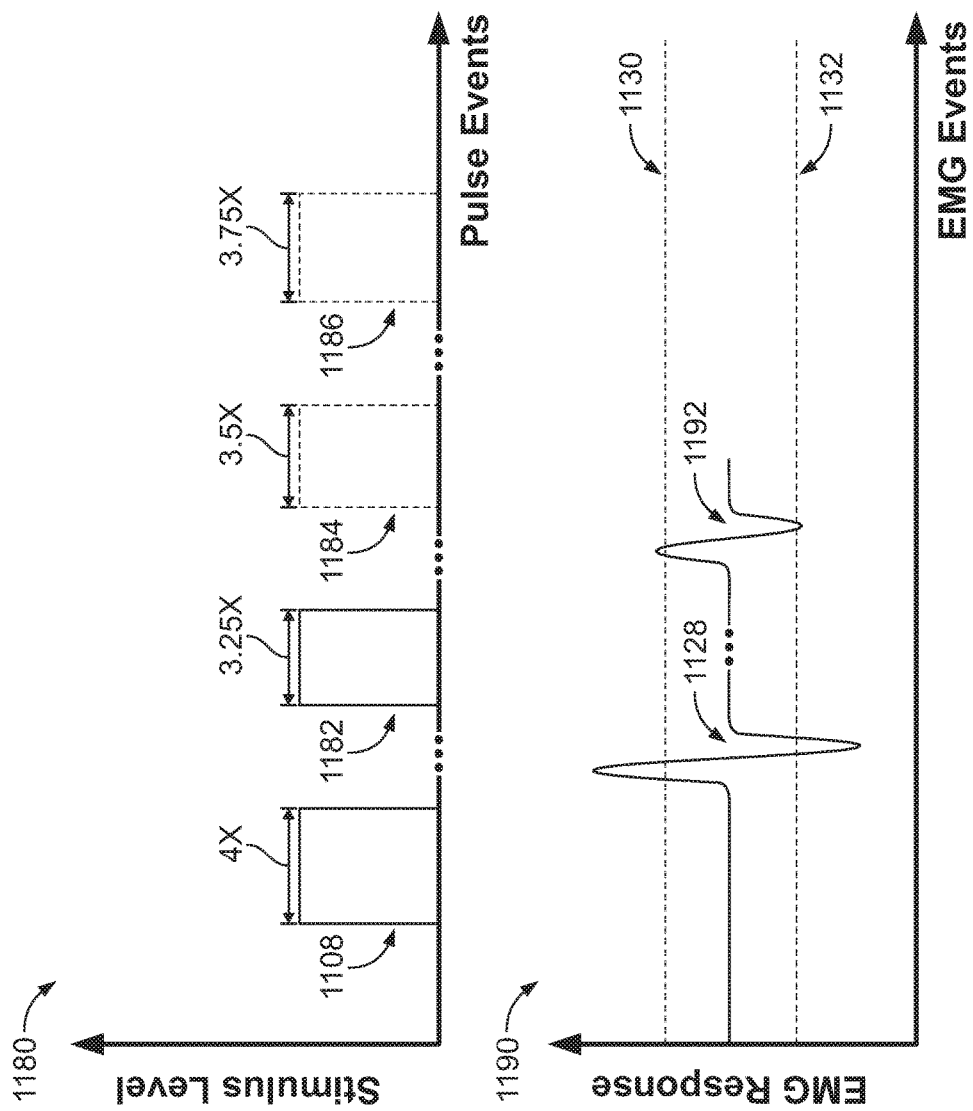

Stimulus 1106, having a pulse width of 3×, elicits a response 1126 that does not exceed the thresholds 1130 and 1132, while stimulus 1108, having a pulse width of 4×, elicits a response 1128 that exceeds the thresholds 1130 and 1132. Thus, the minimum pulse width required to elicit a threshold EMG response falls within the range of pulse widths greater than 3× and less than or equal to 4×. In some implementations, the desired resolution may be greater than the range 3×-4×, and the neuromonitoring system may output 4× as the estimated stimulation threshold pulse width. In other implementations, however, the desired resolution may be less than the range 3×-4×, and further stimulation and monitoring is needed to narrow this range. In such cases, the neuromonitoring system may deliver further stimulus signals having pulse widths between 3× and 4× and determine which signals elicit threshold responses until a smaller range having a lower bound that does not elicit a threshold response and an upper bound that does elicit a threshold response is determined and is smaller than the desired resolution. FIGS. 17-19 depict three illustrative approaches for narrowing the 3×-4× pulse width window until it is within a desired resolution of 0.25×, smaller than the 1× initial pulse width range from 3×-4×.

FIG. 17 shows a graph 1140 of stimulus signals and a graph 1150 of corresponding EMG responses used to narrow the 3×-4× pulse width range until it is less than or equal to the desired 0.25× resolution. Following the pulse 1108 and corresponding response 1128, the neuromonitoring system delivers a stimulus 1142 at a pulse width of 3.5×, cutting the 3×-4× range in half. If a threshold EMG response is detected following the stimulus 1142, then the desired minimum pulse width is determined to lie within the narrower range 3×-3.5×, while a lack of an EMG response following the stimulus 1142 narrows the range to 3.5×-4×. The detected response 1152 following the stimulus 1142 exceeds the thresholds 1130 and 1132, and thus the range containing the minimum threshold is narrowed to 3×-3.5×. The neuromonitoring system again cuts this range in half, and a following stimulus 1144 having a pulse width of 3.25× is delivered. The EMG response 1154 then determines the final range containing the minimum threshold, as a threshold EMG response narrows the range to 3×-3.25×, and lack of a threshold EMG response narrows the range to 3.25×-3.5×. Both of these ranges are equal to the desired threshold, and thus the neuromonitoring system communicates a threshold of 3.25× if the EMG response exceeds the EMG thresholds 1130 and 1132 or communicates a threshold of 3.5× if the EMG response does not exceed the EMG thresholds. As shown in graph 1150, the response 1154 exceeds the EMG thresholds 1130 and 1132, and thus the neuromonitoring system reports a determined minimum threshold pulse width of 3.25×.

Rather than cutting the 3×-4× pulse width range in half, sometimes referred to as bisection, until a suitable range is determined, a neuromonitoring system may deliver stimuli within the range that decrease or increase by an amount equal to the desired resolution until a range is determined that is equal to the resolution, has a lower bound that does not elicit a threshold EMG response, and has an upper bound that elicits a threshold EMG response. FIG. 18 shows a narrowing approach that begins with the 4× stimulus 1108 in graph 1160, which elicits the threshold EMG response 1128 in graph 1170, and decreases the stimulus pulse width by 0.25×, the desired resolution, until a final range is determined. After the stimulus 1108, the pulse width of the next stimulus 1162 is decreased by 0.25× to 3.75×. A subsequent response 1172 meets the EMG thresholds 1130 and 1132, and the range of pulse widths containing the minimum threshold is narrowed to 3×-3.75×, which is still larger than the 0.25× resolution. The next stimulus 1164 has a pulse width that is again decreased by the 0.25× decrement to 3.5×, and the resulting response 1174 again exceeds the thresholds 1130 and 1132.

Following the stimulus 1164, stimulus 1166 is delivered having a pulse width of 3.25×. The stimulus 1166 is the last stimulus needed to narrow the range containing the threshold to a width of 0.25×, and thus a maximum of three subsequent pulses is required to narrow the range to the desired resolution after the threshold EMG response 1128 is detected. As shown in graph 1170, the subsequent response 1176 exceeds the thresholds 1130 and 1132, and thus the neuromonitoring system reports 3.25× as the determined minimum pulse width threshold.

While FIG. 18 illustrates an approach that begins at the upper bound of the initial pulse width range and decreases by an amount equal to the desired resolution, the final range can also be determined by starting at the lower bound of the initial range. This approach is shown in FIG. 19, which depicts stimulus signals in graph 1180 and corresponding EMG responses in graph 1190. After the stimulus 1108 and threshold EMG response 1128, the neuromonitoring system begins at the lower bound of the initial range, 3×, and increments by the resolution, 0.25×, delivering a stimulus 1182 having a pulse width of 3.25×. The resulting EMG response 1192 exceeds the threshold 1130 and 1132, and thus the pulse width range of 3×-3.25× is determined to include the minimum threshold pulse width range. As a result, a minimum of one subsequent stimulus pulse may result in determining the threshold within an acceptable resolution in either the decrementing approach of FIG. 18 or incrementing approach of FIG. 19. If however, the response to stimulus 1182 was not a threshold EMG response, subsequent stimuli 1184 and 1186 are delivered having pulse widths of 3.5× and 3.75× until a threshold EMG response is detected, and the stimulus eliciting that response is reported as the minimum threshold. If no threshold EMG response has been detected following the 3.75× stimulus, the neuromonitoring system reports 4× as the minimum threshold pulse width.

During neuromonitoring, determined thresholds and underlying EMG and stimulus data are continuously presented to a Surgeon. The displays used can provide a customizable interface for a Surgeon or other Professional to control the displayed data. Illustrative examples of such displays are shown in FIGS. 20-34.

Figure 20:
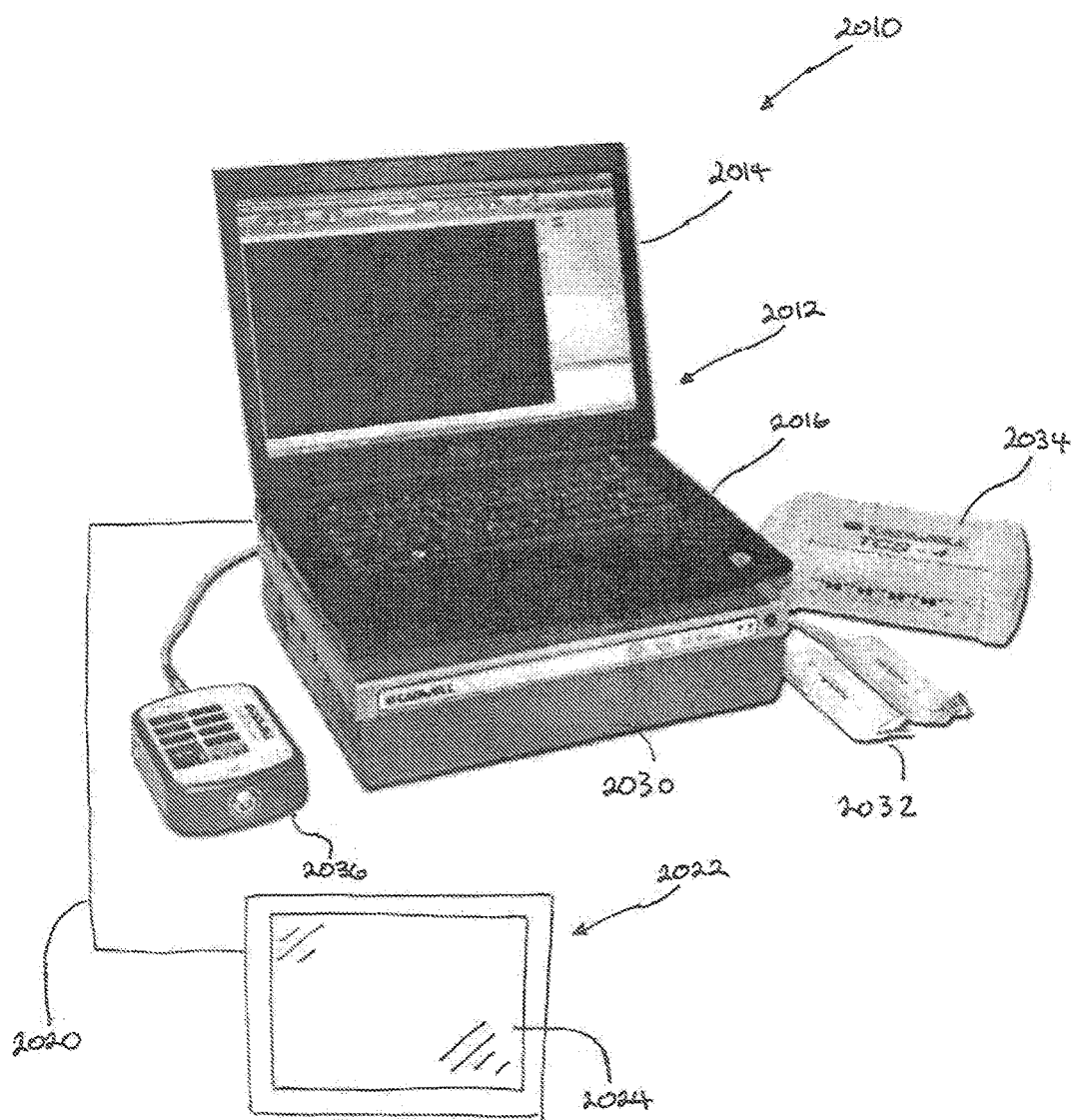
FIG. 20 depicts an illustrative surgical monitoring system.

FIG. 20 shows a surgical monitoring system 2010 according to certain embodiments. The surgical monitoring system 2010 includes a display device 2012 having a monitor or display 2014 and a user interface 2016 for receiving user commands, although in certain embodiments the display 2014 includes a touch-screen interface for receiving user inputs. The display device 2012 is communicatively coupled to a second display device 2022 using a data link 2020 that may be a physical connection or a wireless connection. For example, the display devices 2012, 2022 may be connected to each other by a communication medium, such as a USB port, serial port cable, a coaxial cable, an Ethernet type cable, a telephone line, a radio frequency transceiver or other similar wireless or wired medium or combination of the foregoing. The communication between the display devices 2012, 2022, and any of the other components in FIG. 20, can follow various known communication protocols, such as TCP/IP, cellular protocols including GSM, Wi-Fi, Wi-Max, or other wireless communications technologies or combination of wired or wireless channels. The second display device 2022 includes a monitor or display 2024 that may be configured with a touch-screen interface for receiving user inputs or, alternatively or additionally, may be provided with a user interface similar to the user interface 2016 shown for the first display device 2012. In certain embodiments, the display 2024 of the second display device 2022 need not include a user input interface.

The display device 2012 is coupled to a base unit 2030, and one or more of a remote amplifier 2032, 16-channel external amplifier 2034, and stimulator splitter 2036 (e.g., a EX-IX stimulator) for measuring and displaying the electrical signals generated by muscles, the central nervous system, and/or the peripheral nerves.

Figure 21:
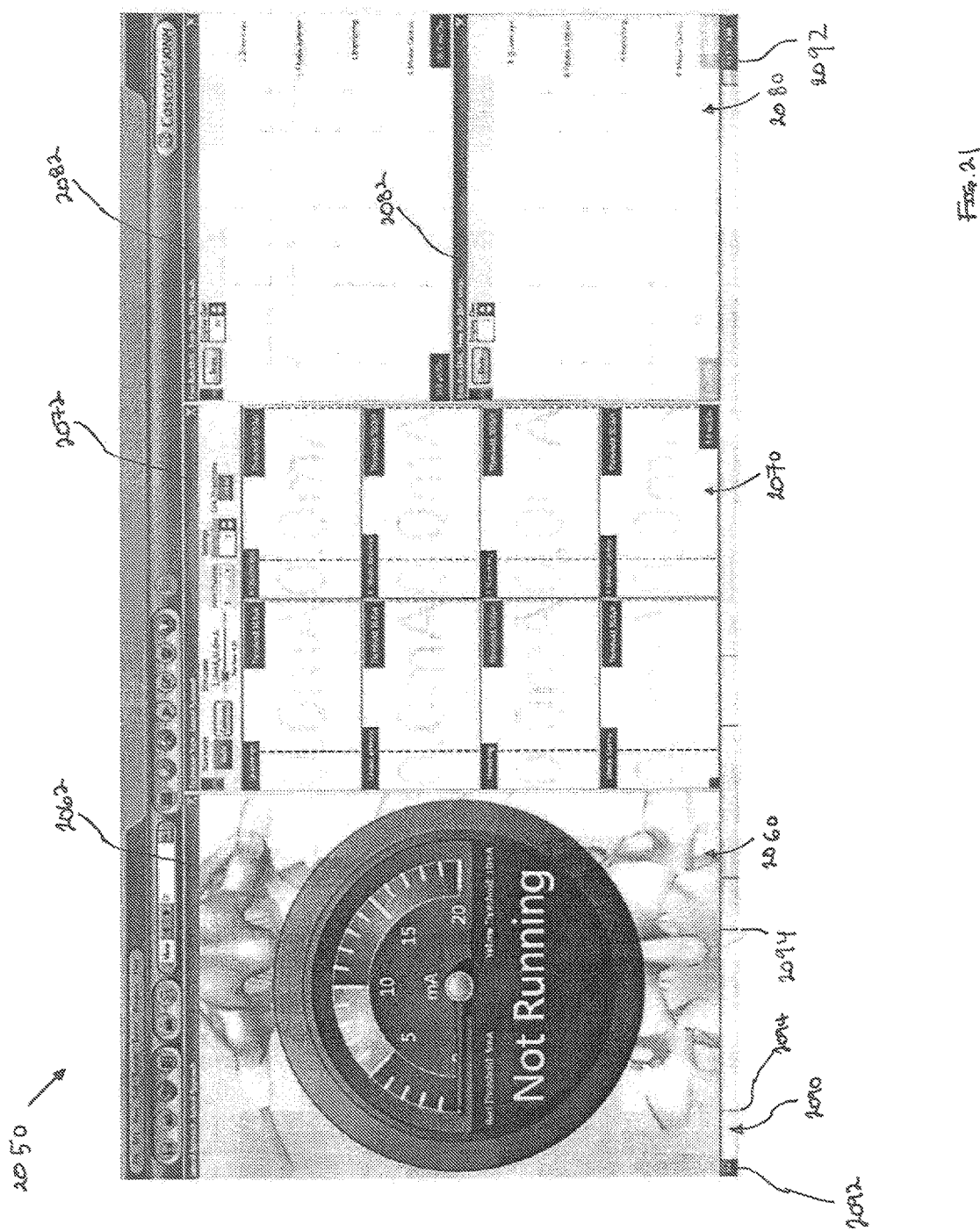
FIG. 21 depicts an illustrative display screen having various mode windows.

FIG. 21 shows an illustrative display screen 2050 according to certain embodiments. As discussed above, certain display screens can be integrated to include both the monitorist views and the surgeon views. The display screen 2050 includes various windows that display physiological data for a patient according to different modes, including a surgeon window 2060, technician or monitorist window 2070, and right and left EMG windows 2080, and further includes an event timeline 2090 along the bottom of the screen. The event timeline 2090 includes a right and left arrow 2092 for moving between each of the events 2094 along the timeline. Each of the windows 2060, 2070, 2080 has a window title bar 2062, 2072, 2082 across the top of the respective window that allows the windows to be docked and undocked from the display screen 2050 and placed in any position on a monitor controlled by the monitoring system 2010. For example, docking and undocking the surgeon window 2060 allows that window to be displayed for the surgeon on a separate monitor such as that provided by the second display device 2022 of FIG. 20. The windows may be undocked by grabbing the window title bar using a cursor controlled by a mouse or other input device, including user touch-screen commands, and then moving the window to any position on a monitor controlled by the monitoring system 2010.

Figure 22:
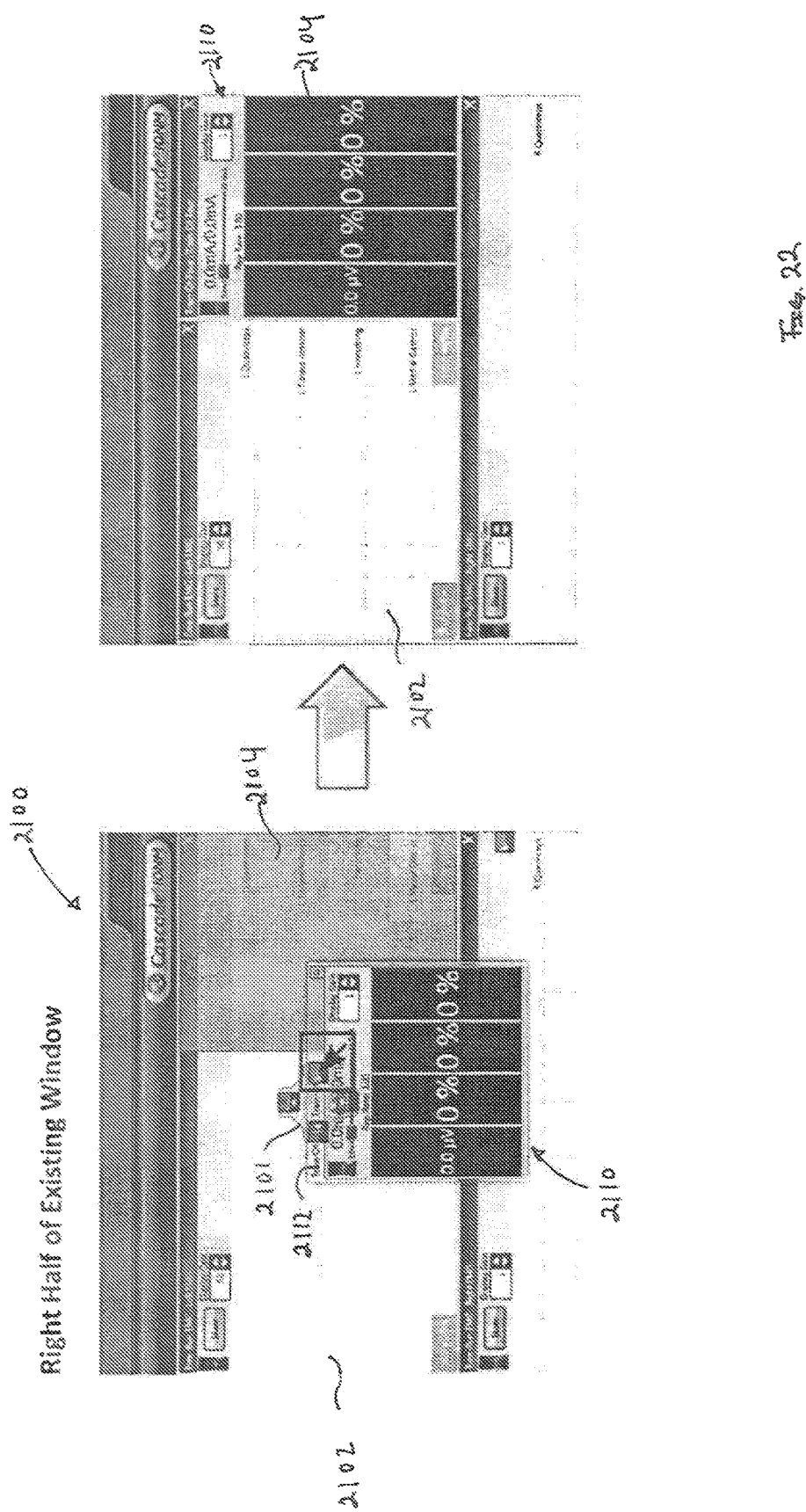
FIGS. 22-24 depict illustrative display screens having mode windows docked to various regions within the respective display screens.
Figure 23:
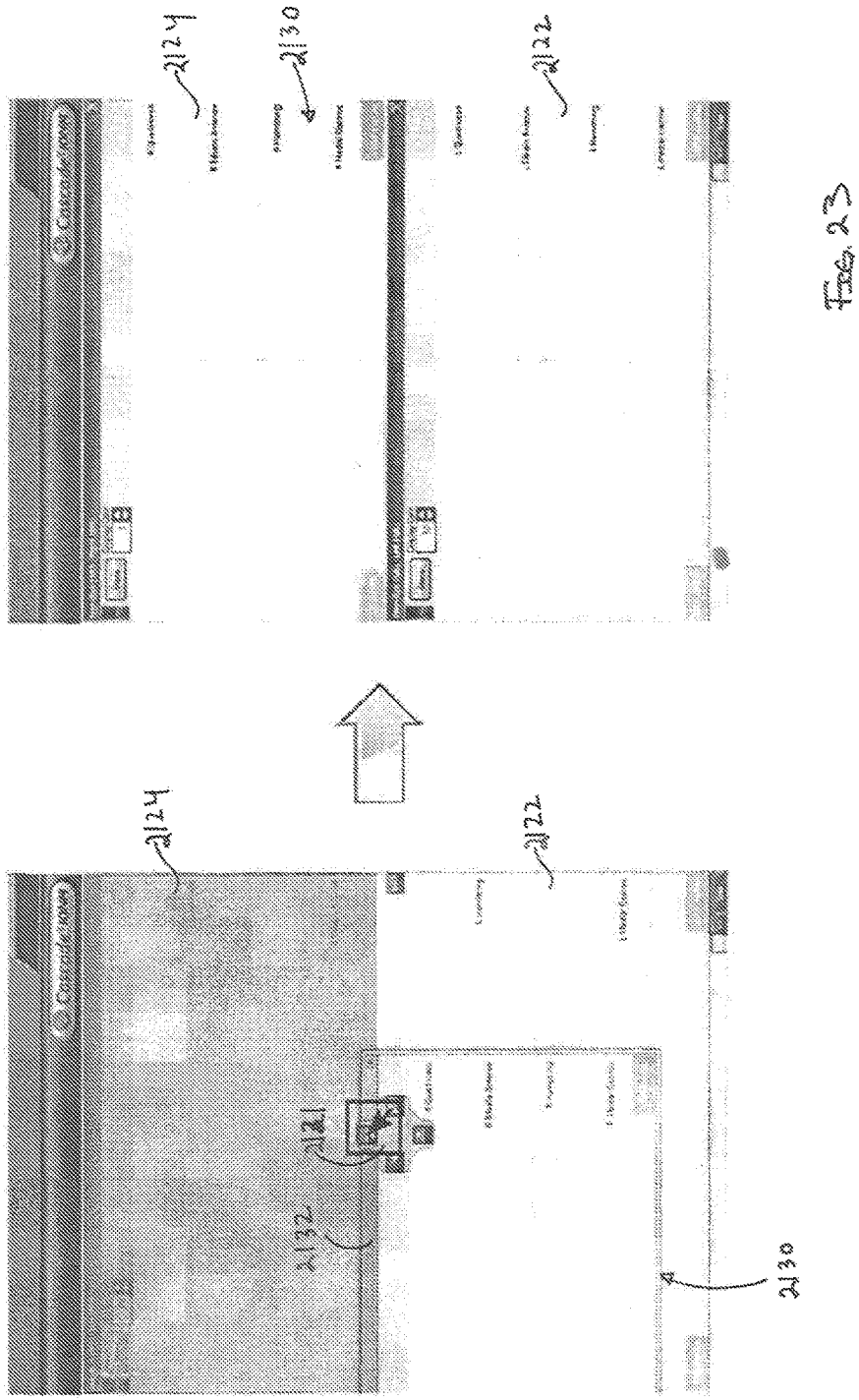
Figure 24:
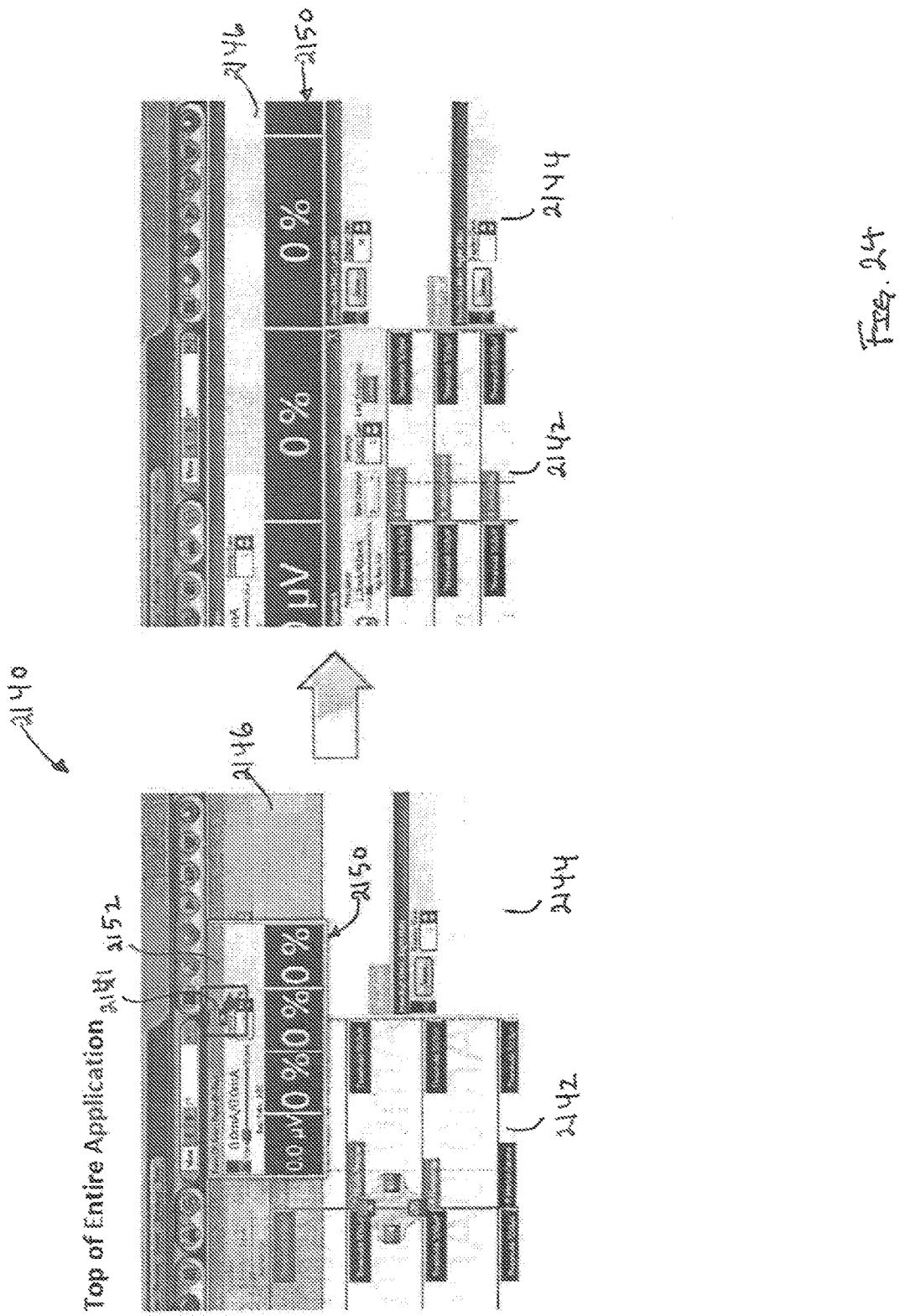

In certain embodiments, to dock an undocked window into a particular region on the display screen, a docking tool is provided that includes a set of arrows that appear when the title bar for that window is selected with the cursor. The potential docking regions for that window will be shadowed in the display screen, and hovering the cursor over different arrows of the docking tool allows the user to see the different docking regions that are available. When a desired docking location is identified, the user releases the title bar and the window becomes docked at the desired docking position. For example, as shown in FIG. 22, a display screen 2100 includes a left region 2102 and blank right region 2104 into which the mode window 2110 may be docked. When the cursor is positioned over the right arrow of the docking tool 2101 and the window title bar 2112 is released, the mode window 2110 is docked into the right region 2104 of the display screen 2100. Similarly, as shown in FIG. 23, a display screen 2120 includes a bottom region 2122 and a blank top region 2124 into which the mode window 2130 may be docked. When the cursor is positioned over the top arrow of the docking tool 2121 and the window title bar 2132 is released, the mode window 2130 is docked into the top region 2124 of the display screen 2120. As shown in FIG. 24, a mode window can be docked along the top of a display screen 2140 having multiple windows. The display screen 2140 includes left and right bottom regions 2142, 2144 and a blank top region 2146 into which the mode window 2150 may be docked. When the cursor is positioned over the top arrow of the docking tool 2141 and the window title bar 2152 is released, the mode window 2150 is docked into the top region 2146 of the display screen 2140.

As discussed above, the surgical monitoring system allows for simultaneous surgeon and monitorist views of data that is recorded by a nerve detection algorithm. In certain embodiments, this dual-view feature can be implemented by undocking the surgeon window 2060 from the integrated view of display screen 2050 of FIG. 21 and placing the surgeon window 2060 into a second, surgeon-facing, monitor on the second display device 2022. It will be understood that any suitable technique may be used to cause the first and second display devices 2012, 2022 to display the surgeon and monitorist views and that docking and undocking the windows is merely exemplary. In particular, any technique for modifying or otherwise customizing the displays to provide different but simultaneous presentation of a neuromuscular response on different screens may be used. In certain embodiments, the nature of the information displayed in the two (or more) displays depends on a user-selected indication (or automatically determined designation) of the type of user (e.g., monitorist or surgeon).

Figure 25:
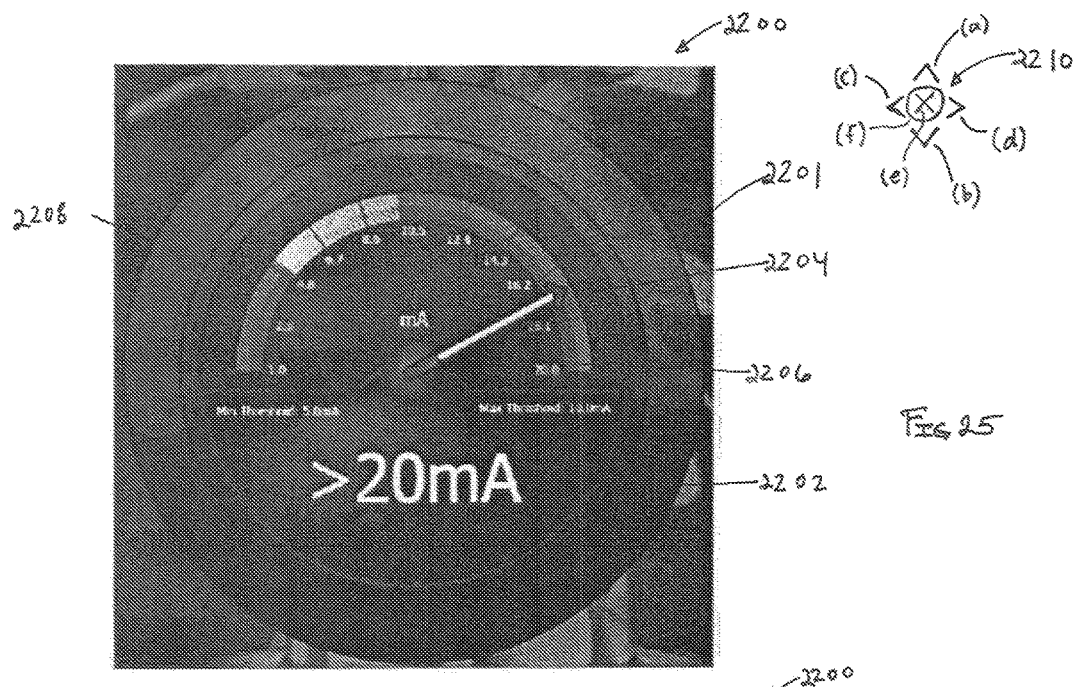
FIGS. 25 and 26 depict various illustrative displays for use with the surgeon view.
Figure 26:
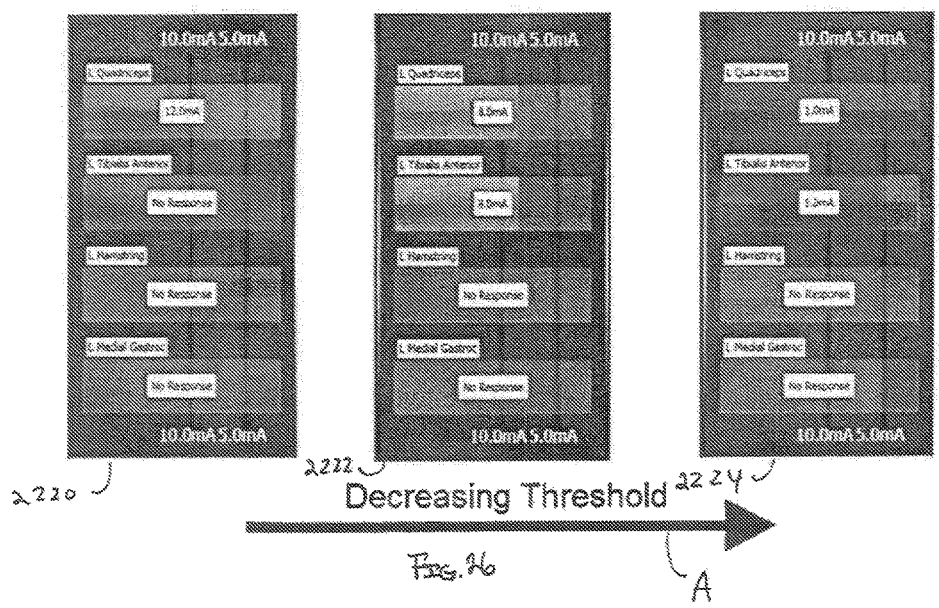

The surgeon view displays information in a relatively simple and easy-to-read manner. For example, as discussed above, the monitorist view may include the waveform responses to the current stimulus while the surgeon view does not; instead including numeric and/or graphical indicators of distance and or current amplitude based on the same waveform responses. In certain embodiments, the surgeon view 2200 displays information to the surgeon in two respects. First, as shown in FIG. 25, the surgeon view includes a dial 2201 that indicates the lowest current threshold value for any sensed muscle at that given point in time. The dial 2201 includes the threshold value in large text 2202 and a gauge arrow 2204 that points to the threshold value on a semi-circular scale 2206. The background color 2208 of the dial 2201 may change according to predetermined range definitions. In certain embodiments, the predetermined range definitions may be configured in a setup screen discussed in detail in FIG. 34. Second, as shown in FIG. 26, the surgeon view 2200 displays the individual muscle thresholds via horizontal bar graphs 2220, 2222, 2224 on the left and right sides (or on any other suitable side) of the dial 2201. As the threshold for activating a muscle response decreases, the bar increases in size along the direction A shown by the decreasing threshold arrow. In certain embodiments, the bar 2220, 2222, 2224 changes from green to yellow to red (or any other suitable color), as the threshold decreases through the threshold ranges. In certain embodiments, the surgeon dial windows are user-configurable to change the relative size of the respective windows.

In certain embodiments, the dial 2201 can be used to indicate to the surgeon the absolute distance to a proximal nerve. Similar to the manner in which the dial 2201 indicates the lowest threshold for any sensed muscle, the dial 2201 may include the distance value in large text 2202 and a gauge arrow 2204 that points to the distance value on a semi-circular scale 2206. The background color 2208 of the dial 2201 may change according to predetermined range definitions. In certain embodiments, the predetermined range definitions may be configured in a setup screen.

Furthermore, in certain embodiments, the dial 2201 can be used to indicate to the surgeon the direction of a proximal nerve. For example, a directional indicator 2210 may be displayed with the dial 2201 to indicate the relative direction of the proximal nerve with respect to the travel of the probe in three-dimensions including superior (a), inferior (b), medial (c), lateral (d), anterior (e), and posterior (f) directional indicators. Any suitable technique may be used for determining the location of a nerve. Mapping the location of nerves is discussed in detail in Cadwell U.S. Patent Application Publication No. 2012/0109004, filed Oct. 27, 2010, the disclosure of which is hereby incorporated by reference herein in its entirety.

Various surgeon views 2260, 2270, 2280, 2290 are depicted in FIGS. 27-30 to illustrate exemplary changes to the dial that can occur during a surgical procedure. As shown in FIG. 27, when the selected surgical mode is running but the stimulus loop is not closed (e.g., the probe or other instrument is not touching the patient), the dial indicates "No Stim." As shown in FIG. 28, when the stimulus loop is closed, but the algorithm has not yet identified a threshold, the dial indicates "Searching." As shown in FIG. 29, when the algorithm reaches its maximum stimulus level without identifying a threshold, the dials indicates ">MAX," where MAX is the maximum stimulus level for the mode, depicted as 20 mA in the figure. As shown in FIG. 30, when the algorithm has detected the minimum level required to produce a threshold crossing, that level is displayed and the background color of the dial may be adjusted as necessary.

Figure 31:
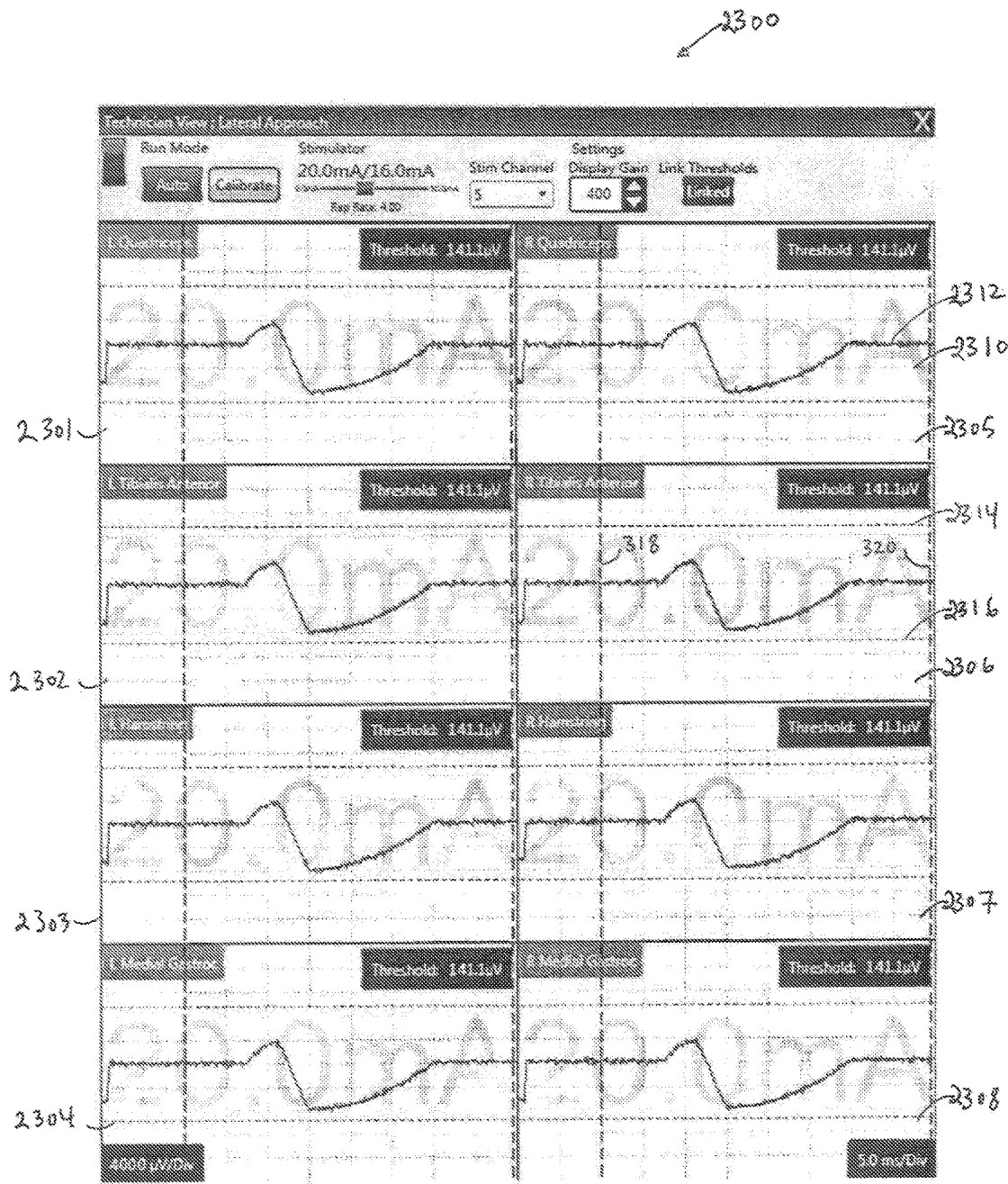
FIG. 31 depicts an illustrative display for use with the monitorist view.

The monitorist view displays detailed information to the technician or monitorist, including the raw waveform responses for each sensed muscle. As discussed above, the monitorist view may include the waveform responses to the current stimulus while the surgeon view does not; instead including numeric and/or graphical indicators of distance and or current amplitude based on the same waveform responses. The detailed information provided to the monitorist allows the monitorist to determine, for example, whether the information is reliable (e.g., by checking for artifacts or other signal noise) and adjust the settings of the monitoring system pre, post, or intraoperatively. As shown in FIG. 31, for example, the monitorist view 2300 includes waveform responses and each sensed muscle has its own sub-window in the monitorist view. Eight sub-windows 2301-2308 are shown in the figure, one for each sensed muscle of the right and left leg, although any suitable number of sub-windows may be used. Responses within the monitorist view 2300 are updated approximately once per second. The stimulus level associated with each waveform is displayed via a colored watermark 2310 in the background of the window 2305 for that muscle. The waveforms displayed in each window (e.g., waveform 2312 of window 2305) may be determined based on a "threshold crossing" or a "response to last stimulus." A threshold crossing occurs if the corresponding muscle evoked a suprathreshold response, and in such cases the response at the threshold value is displayed. A response to last stimulus occurs if the corresponding muscle did not evoke a suprathreshold response, and in such cases the response at the highest stimulus level is displayed. As an example, assume that the algorithm stimulated at 5, 6, 7, 8, and 9 mA during the one second period. The left quadriceps crossed the threshold at 6 mA, but none of the other muscles responded to any of the stimulus pulses. The left quad window would display its response at 6 mA, while the other muscle windows would display their responses at 9 mA. It is understood that displays are referred to as "monitorist views" or "surgeon views" in order to simplify the discussion and that any specific display may be viewed by a monitorist, surgeon, or other personnel associated with the surgical procedure.

Figure 32:
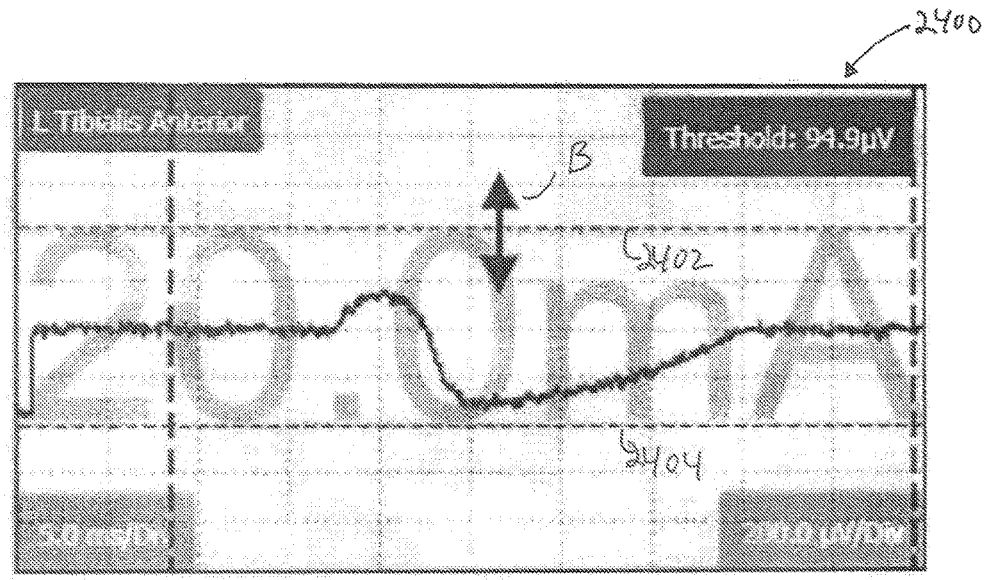
FIG. 32 depicts an illustrative sub-window indicating the response amplitude threshold.

Within the windows 2301-2308 for each muscle, there is a pair of horizontal dashed lines (e.g., lines 2314 and 2316 of window 2306) that represent the response amplitude threshold for that muscle. Responses that cross this dashed line in either the positive or negative direction will be counted by the algorithm as threshold responses. In certain embodiments, each channel has an independent response amplitude threshold. The response amplitude threshold can be adjusted by selecting one of the horizontal dashed lines and moving it up or down. The new response amplitude threshold level is indicated by the decorator in the top-right corner of that window. As shown in FIG. 32, the dashed lines 2402, 2404 of a given sub-window 2400 can be moved up or down along the directions of arrow B.

Figure 33:
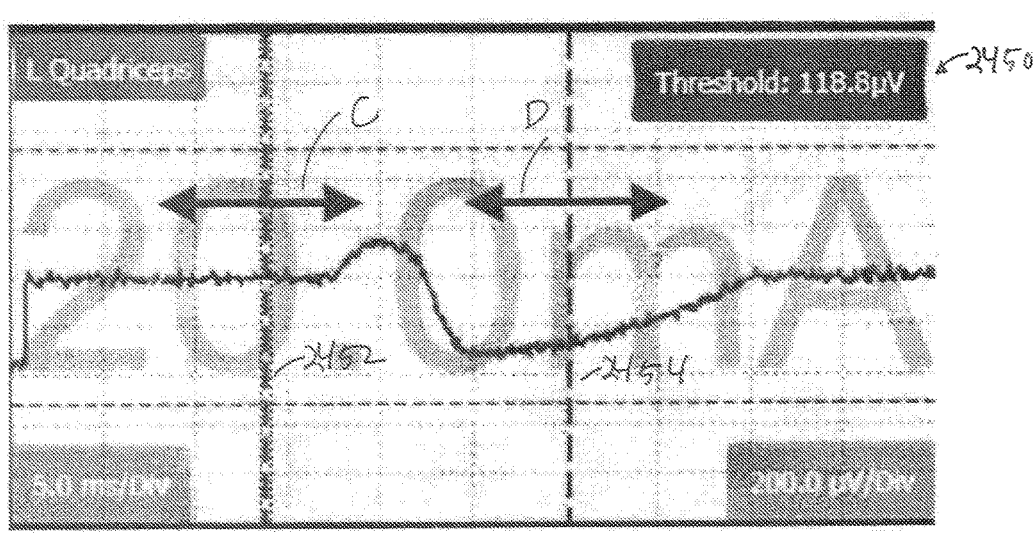
FIG. 33 depicts an illustrative sub-window for artifact rejection.

Within the windows 2301-2308 for each muscle, there is also a pair of vertical dashed lines (e.g., lines 2318 and 2320 of window 2306) that represent periods of time that are ignored by the algorithm. Specifically, any threshold crossings that occur before the left-most dashed line 2318 are considered stimulus artifact and not a true muscle response. Any threshold crossings that occur after the right-most dashed line 2320 are considered baseline drift artifact and not a true muscle response. As shown in FIG. 33, the dashed lines 2452, 2454 of a given sub-window 2450 can be moved along the directions of arrows C and D.

Figure 34:
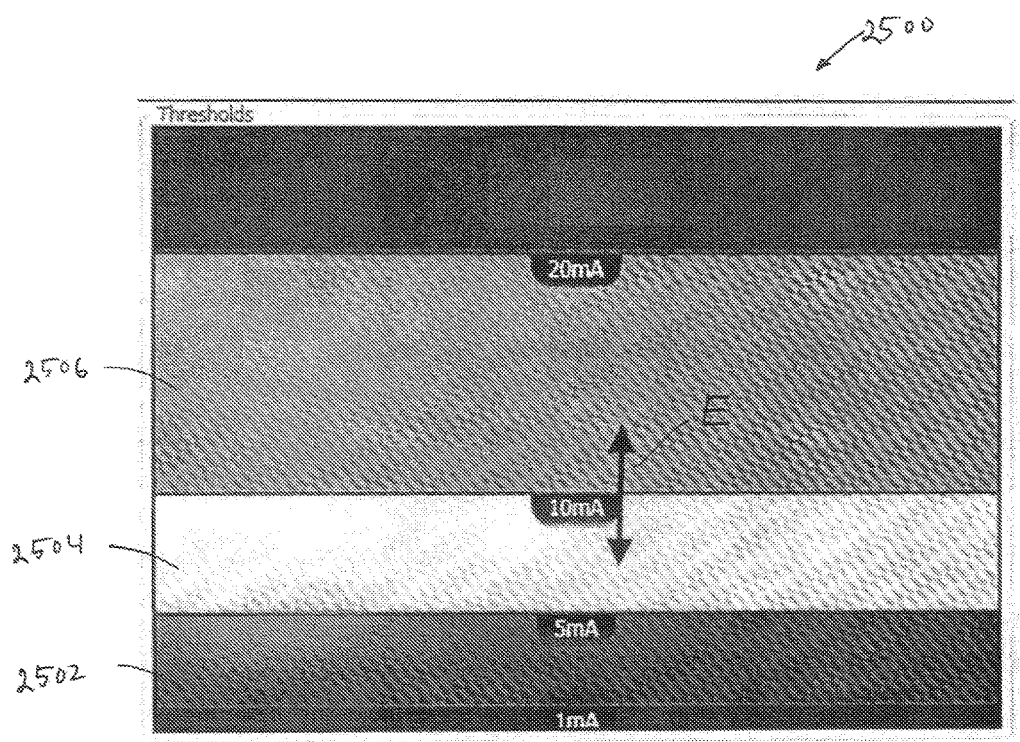
FIG. 34 depicts an illustrative interface for adjusting threshold ranges.

In certain embodiments, threshold ranges are used to determine the colors displayed on the surgeon dial view and the audio tones that are played during the surgical procedure. These ranges can be adjusted by the monitorist or the surgeon. Any suitable threshold ranges may be used. For example, in certain embodiments where the maximum stimulus level is set at 20 mA, default threshold ranges of 0-5 mA, 5-10 mA, and greater than 10 mA may be used for color indications that are red, yellow, and green, respectively. Audio tones may accompany the procedure, and in certain embodiments a green threshold results in a single tone that repeats once every two seconds. For the yellow threshold, a single tone is produced at a relatively higher pitch, level, and repetition rate than the green tone. For the red threshold, a single tone is produced at a high pitch, level, and repetition rate than the yellow tone. It will be understood that any suitable color and/or audio scheme can be used to provide feedback to the surgeon during the surgical approach. As shown in FIG. 34, a threshold display screen 2500 may be displayed that allows the user to change the threshold ranges for the red 2502, yellow 2504, and green 2506 zones. In certain embodiments, the user can slide the respective threshold values up or down along the directions of arrow E. In certain embodiments, the user can change the threshold values by manually entering the desired threshold values (e.g., using the user interface 2016 of FIG. 20).

The foregoing is merely illustrative of the principles of the disclosure, and the systems, devices, and methods can be practiced by other than the described embodiments, which are presented for purposes of illustration and not of limitation. It is to be understood that the systems, devices, and methods disclosed herein, while shown for use in spinal surgical procedures, may be applied to systems, devices, and methods to be used in other surgical procedures performed in the proximity of neural structures where nerve avoidance, detection, or mapping is desired, including, but not limited to selected brain surgeries, carotid endarterectomy, otolaryngology procedures such as acoustic neuroma resection, parotidectomy, nerve surgery, or any other surgical procedures.

Variations and modifications will occur to those of skill in the art after reviewing this disclosure. The disclosed features may be implemented, in any combination and subcombination (including multiple dependent combinations and subcombinations), with one or more other features described herein. The various features described or illustrated above, including any components thereof, may be combined or integrated in other systems. Moreover, certain features may be omitted or not implemented.

Examples of changes, substitutions, and alterations are ascertainable by one skilled in the art and could be made without departing from the scope of the information disclosed herein. All references cited herein are incorporated by reference in their entirety and made part of this application.

What is claimed is:

1. A method for neuromonitoring, comprising:
   delivering a first stimulus signal having a first pulse width and a second stimulus signal having a second pulse width to tissue including or adjacent to a nerve, the first pulse width being different from the second pulse width;
   detecting, in muscle tissue, a first neuromuscular response in response to the first stimulus signal and a second neuromuscular response in response to the second stimulus signal;
   determining a stimulation threshold for the nerve from the first and second pulse widths and the first and second neuromuscular responses, the stimulation threshold being an estimate of a minimum pulse width required to elicit a neuromuscular response greater than or equal to a predetermined threshold, wherein the stimulation threshold is different from the first and second pulse widths; and
   communicating to a user an indicator of the stimulation threshold to indicate at least one of nerve proximity and pedicle integrity.

2. The method of claim 1, wherein the first and second stimulus signals are delivered at a constant current.

3. The method of claim 1, wherein the first and second stimulus signals are delivered at a constant voltage.

4. The method of claim 1, further comprising delivering a plurality of stimulus signals, each stimulus signal having a larger pulse width than a preceding stimulus signal.

5. The method of claim 4, wherein the pulse width of the stimulus signals in the plurality of stimulus signals increase at a constant increment.

6. The method of claim 4, wherein the pulse width of the stimulus signals in the plurality of stimulus signals increase at varying increments.

7. The method of claim 4, wherein delivering the plurality of stimulus signals comprises delivering stimulus signals until a neuromuscular response greater than or equal to the predetermined threshold is detected.

8. The method of claim 1, wherein the second neuromuscular response is the first detected neuromuscular response greater than or equal to the predetermined threshold.

9. The method of claim 1, wherein communicating an indicator comprises communicating the second pulse width to the user.

10. The method of claim 1, wherein the first and second pulse widths define an initial pulse width range, and determining the stimulation threshold comprises delivering stimulus signals having pulse widths selected from within the initial pulse width range to determine the minimum pulse width required to elicit a neuromuscular response greater than or equal to the predetermined threshold.

11. The method of claim 10, wherein delivering stimulus signals having pulse widths selected from within the initial pulse width range comprises delivering a sequence of stimulus signals having pulse widths that either increase by a constant increment or decrease by a constant decrement.

12. The method of claim 11, further comprising delivering the sequence of stimulus signals from a first stimulus signal near a lower bound of the initial pulse width range and increasing the pulse width of subsequent stimulus signals to a value near an upper bound of the initial pulse width range.

13. The method of claim 11, further comprising delivering the sequence of stimulus signals from a first stimulus signal near an upper bound of the initial pulse width range and decreasing the pulse width of subsequent stimulus signals to a value near a lower bound of the initial pulse width range.

14. The method of claim 10, further comprising delivering a subsequent stimulus pulse having a pulse width equal to a midpoint of the initial pulse width range.

15. The method of claim 9 wherein communicating the indicator comprises displaying an indication of electric charge.

16. The method of claim 15, wherein the indication of electric charge is displayed in coulombs.

17. The method of claim 9, wherein communicating the indicator comprises displaying a distance between the nerve and a surgical instrument.

18. The method of claim 17, further comprising calculating the displayed distance from an electric charge corresponding to the stimulation threshold.

19. The method of claim 9, wherein communicating the indicator comprises displaying a pulse width corresponding to the stimulation threshold.

20. The method of claim 1, further comprising communicating at least one of a constant current or a constant voltage at which the first and second stimulus signals are delivered.

21. The method of claim 1, wherein the first neuromuscular response is detected before the second stimulus signal is delivered.

22. The method of claim 1, wherein the second stimulus pulse is delivered before the first neuromuscular response is detected.

23. The method of claim 1, wherein an offset time between delivery of the first stimulus pulse and delivery of the second stimulus pulse is greater than or equal to a refractory period associated with the nerve and the muscle tissue.

24. A method for neuromonitoring, comprising:
   delivering by a stimulating electrode located on a surgical accessory first and second stimulation signals to tissue including or adjacent to a nerve;
   detecting by a sensor associated with muscle tissue associated with the nerve respective first and second neuromuscular responses elicited by the first and second stimulation signals;
   calculating a stimulation threshold for the nerve by extrapolation from the respective first and second neuromuscular responses, wherein the stimulation threshold is different from the first and second stimulation signals; and
   communicating an indicator of the stimulation threshold to a user to indicate one of nerve proximity and pedicle integrity.

25. The method of claim 24, wherein delivering the first and second stimulation signals comprises delivering the first and second stimulation signals each having a different amplitude.

26. The method of claim 24, wherein delivering the first and second stimulation signals comprises delivering the first and second signals each having a different pulse width.

* * * * *